US008080253B2

(12) United States Patent
Kaumaya et al.

(10) Patent No.: US 8,080,253 B2
(45) Date of Patent: Dec. 20, 2011

(54) CHIMERIC VEGF PEPTIDES

(75) Inventors: Pravin Kaumaya, Westerville, OH (US); David Cohn, Bexley, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 404 days.

(21) Appl. No.: 11/052,721

(22) Filed: Feb. 7, 2005

(65) Prior Publication Data

US 2005/0233964 A1    Oct. 20, 2005

Related U.S. Application Data

(60) Provisional application No. 60/542,041, filed on Feb. 5, 2004.

(51) Int. Cl.
*A61K 39/00* (2006.01)
*A61K 38/18* (2006.01)
*C07H 21/04* (2006.01)

(52) U.S. Cl. ............... 424/192.1; 424/184.1; 424/185.1; 514/8.1; 536/23.4

(58) Field of Classification Search ........................ None
See application file for complete search history.

(56) References Cited

U.S. PATENT DOCUMENTS

| | | | | |
|---|---|---|---|---|
| 6,339,139 | B1 * | 1/2002 | Gu et al. ........................ | 530/300 |
| 7,060,284 | B1 * | 6/2006 | Kaumaya et al. .......... | 424/277.1 |
| 2006/0110400 | A1 * | 5/2006 | Glover et al. .............. | 424/185.1 |

FOREIGN PATENT DOCUMENTS

| | | |
|---|---|---|
| WO | WO 94/00153 | 1/1994 |
| WO | WO 95/17210 | 6/1995 |
| WO | WO 96/02555 | 2/1996 |
| WO | WO 96/33739 | 10/1996 |
| WO | 0034337 A1 | 6/2000 |
| WO | 2005/076972 A2 | 8/2005 |

OTHER PUBLICATIONS

Boocock et al. "Expression of vascular endothelial growth factor and its receptors flt and KDR in ovarian carcinoma", *J Natl Cancer Inst* (1995) vol. 87, pp. 506-516.
Chou et al.,, "Prediction of the secondary structure of proteins from their amino acid sequence", *Adv. Enzymol. Relat. Subj. Biochem.* (1978) vol. 47, pp. 45-148.
Cole et al., "The EBV-Hybridoma Technique and its Application to Human Lung Cancer" in *Monoclonal Antibodies and Cancer Therapy* (Alan R. Liss, Inc., 1985) pp. 77-96.
Dakappagari et al., "Prevention of Mammary Tumors with a Chimeric HER-2 B-cell Epitope Peptide Vaccine", *Cancer Research* (2000) vol. 60, pp. 3782-3789.
Deulofeut et al., "Cellular recognition and HLA restriction of a midsequence HBsAg peptide in hepatitis B vaccinated individuals", *Mol Immunol* (1993) vol. 30, pp. 941-948.
Gentz et al., "Bioassay for trans-activation using purified human immunodeficiency virus *tat*-encoded protein: Trans-activation requires mRNA synthesis", *Proc. Natl. Acad. Sci. USA* (1989) vol. 86, pp. 821-824.

Gordon et al., "Phase I safety and pharmacokinetic study of recombinant human anti-vascular endothelial growth factor in patients with advanced cancer", *J Clin Oncol* (2001) vol. 19, pp. 843-850.
Hanahan et al., "Patterns and emerging mechanisms of the angiogenic switch during tumorigenesis". *Cell* 1996;86:353-64.
Hollingsworth et al., "Tumor angiogenesis in advanced stage ovarian carcinoma", *Am J Pathol* (1995) vol. 147, pp. 33-41.
Hopp et al., "Prediction of protein antigenic determinants from amino acid sequences", *Proc. Natl. Acad. Sci. USA* (1981) vol. 78, No. 6, pp. 3824-3828.
Jemal et al., "Cancer Statistics, 2003", *CA Cancer J Clin* (2003) vol. 53, pp. 5-26.
Karplus et al., "Prediction of Chain Flexibility in Proteins, A Tool for the Selection of Peptide Antigens", *Naturwiss* (1985) vol. 72, pp. 212-213.
Kaumaya et al., "De novo engineering of protein immunogenic and antigenic determinants", in *Peptides* (Basava and Anantharamaiah, Ed., Birkauser, Boston, 1994) vol. 9, pp. 133-164.
Kaumaya et al., "Peptide vaccines incorporating a "promiscuous" T-cell epitope bypass certain haplotype restricted immune responses and provide broad spectrum immunogenicity", *J Mol Recognit* (1993) vol. 6, pp. 81-94.
Kaumaya et al., "Synthesis and biophysical characterization of engineered topographic immunogenic determinants with αα topology", *Biochemistry* (1990) vol. 29, pp. 13-23.
Kim et al., "Inhibition of vascular endothelial growth factor-induced angiogenesis suppresses tumour growth in vivo", *Nature* (1993) vol. 362, pp. 841-844.
Kobs-Conrad et al., "Engineered Topographic Determinants with αβ, βαβ, and βαβα Topologies Show High Affinity Binding to Native Protein Antigen (Lactate Dehydrogenase-$C_4$)", *The Journal of Biological Chemistry* (1993) vol. 268, No. 34, pp. 25285-25295.
Kohler et al., "Continuous cultures of fused cells secreting antibody of predefined specificity", *Nature* (1975) vol. 256, pp. 495-497.
Kozbor et al., "The production of monoclonal antibodies from human lymphocytes", *Immunology Today* (1983) vol. 4, pp. 72-79.
LeCouter et al., "Identification of an angiogenic mitogen selective for endocrine gland endothelium", *Nature* (2001) vol. 412, pp. 877-884.
Leung et al., "Vascular endothelial growth factor is a secreted angiogenic mitogen", *Science* (1989), vol. 246, pp. 1306-1309.
Margolin et al., "Phase Ib trial of intravenous recombinant humanized monoclonal antibody to vascular endothelial growth factor in combination with chemotherapy in patients with advanced cancer: Pharmacologic and long-term safety data", *J Clin Oncol* (2001) vol. 19, pp. 851-856.

(Continued)

*Primary Examiner* — Marianne P Allen
(74) *Attorney, Agent, or Firm* — Calfee, Halter & Griswold LLP

(57) ABSTRACT

Compositions for and methods of treating patients with malignancies associated with overexpression of VEGF, particularly ovarian cancer are provided herein. The compositions include but are not limited to certain VEGF epitopes, multivalent peptides comprising the epitopes, and chimeric peptides comprising one or more of the epitopes and a T cell epitope.

4 Claims, 12 Drawing Sheets

OTHER PUBLICATIONS

Markman et al., "Phase III randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial.", *J Clin Oncol* (2003) vol. 21, pp. 2460-2465.

McGuire et al., "Cyclophosphamide and cisplatin compared with paclitaxel and cisplatin in patients with stage III and stage IV ovarian cancer", *N Engl J Med* (1996) vol. 334, pp. 1-6.

Nair et al., "Synergy between tumor immunotherapy and antiangiogenic therapy", *Blood* (2003) vol. 102, No. 3, pp. 964-971.

Olson et al., "Vascular permeability factor gene expression in normal and neoplastic human ovaries", *Cancer Res* (1994) vol. 54, p. 276-80.

Paley et al., "Vascular endothelial growth factor expression in early stage ovarian cancer", *Cancer* (1997) vol. 80, pp. 98-106.

Passaniti et al., "A simple, quantitative method for assessing angiogenesis and antiangiogenic agents using reconstituted basement membrane, heparin, and fibroblast growth factor", *Lab Invest* (1992) vol. 67, No. 519-28.

Peoples et al., "Breast and ovarian cancer-specific cytotoxic T lymphocytes recognize the same HER2/neu-derived peptide", *Proc. Natl. Acad. Sci. USA* (1995) vol. 92, pp. 432-436.

Rose et al., "Hydrophobicity of Amino Acid Residues in Globular Proteins", *Science* (1985) vol. 229, pp. 834-838.

Sakaguchi, "Regulatory T cells: key controllers of immunologic self-tolerance", *Cell* (2000) vol. 101, pp. 455-458.

Tempfer et al., "Vascular endothelial growth factor serum concentrations in ovarian cancer", *Obstet Gynecol* (1998) vol. 92, pp. 360-363.

Thornton et al., "Location of 'continuous' antigenic determinants in the protruding regions of proteins", *EMBO J.* (1986) vol. 5, pp. 409-413.

Wagner et al., "Immunological Consolidation of Ovarian Carcinoma Recurrences with Monoclonal Anti-Idiotype Antibody ACA125: Immune Responses and Sruvival in Palliative Treatment", *Clinical Cancer Research* (2001) vol. 7, pp. 1154-1162.

Wei et al., "Immunogene therapy of tumors with vaccine based on *Xenopus* homologous vascular endothelial growth factor as a model antigen", *PNAS* (2001) vol. 98, No. 20, pp. 11545-11550.

Welling et al., "Prediction of sequential antigenic regions in proteins", *FEBS Lett.* (1985) vol. 188, pp. 215-218.

Wolff et al., "Direct gene transfer into mouse muscle in vivo", *Science* (1990) vol. 247, pp. 1465-1468.

Lu, et al., "Identification of the residues in the extracellular region of KDR important for the interaction with vascular endothelial growth factor and neutralizing anti-KDR antibodies," Journal of Biological Chemistry, (2000), vol. 275, No. 19, pp. 14321-14330.

Yang, et al., "Design and Synthesizing of human vascular endothelial growth factor (VEGF) peptide,"(1999), U.S. National Library of Medicine; Bethesda, MD, US, (English abstract only).

* cited by examiner

A.

B.

← 42 kDa →

VEGF peptide antibody

Ab-4 (VEGF monoclonal Ab)

A.

B.

Optimization of PC/NC

Addition of VEGF peptide antibodies

A.  B.

Matrigel™ and rhVEGF    Matrigel™, rhVEGF and VEGF peptide Abs

A.

B.

A.

B.

|  | Estrous cycle | |
|---|---|---|
|  | pre-treatment | post-treatment |
| Control | 5.15± 0.27 | 4.57±0.32 |
| anti-VEGF | 5.9±0.22 | 1.71±0.21 |

C.

A.

B.

A.

B.

A.

B.

CHIMERIC VEGF PEPTIDES

This application claims priority to U.S. Provisional Application No. 60/542,041, filed Feb. 5, 2004, the entire disclosure of which is incorporated herein by reference.

TECHNICAL FIELD OF THE INVENTION

The present invention relates to compositions for and methods of treating patients with malignancies associated with overexpression of VEGF, particularly ovarian cancer. The compositions of the present invention include certain VEGF epitopes, multivalent peptides comprising said epitopes, and chimeric peptides comprising one or more of said epitopes and a T cell epitope.

BACKGROUND

Ovarian cancer is the most lethal gynecologic malignancy, with almost 14,000 women in the United States expected to die of the disease in 2003 [Jemal]. Unfortunately, there is no effective means for detection of early ovarian cancer, and as such over 75% of cases are diagnosed when the disease has spread to the upper abdomen or lymph nodes. Despite intensive cytotoxic chemotherapy following radical surgery to reduce ovarian cancer volume, the median survival of women with advanced and large-volume ovarian cancer is under 40 months [McGuire].

Recent studies have demonstrated the critical role of angiogenesis in tumor development and the formation of metastatic tumor deposits. The inhibition of tumor angiogenesis has emerged as a promising new therapeutic modality. A number of biologic activities have been identified as being involved in this complex process, however, vascular endothelial growth factor (VEGF) is now known to be one of the most potent and specific pro-angiogenic factors responsible for tumor-induced angiogenesis [Leung], and is the most promising target for inhibition of tumor-induced angiogenesis. VEGF is overexpressed in a number of human solid malignancies, including ovarian cancer [Boocock, Olson]. VEGF overexpression has also been demonstrated in women with ovarian cancer and has been shown to be a poor prognostic factor [Hollingsworth, Paley, Tempfer]. Thus, VEGF is a rational target against which immunization may have a role in the treatment or prevention of ovarian cancer.

Various strategies have been used to inhibit the function of VEGF. These include targeting the VEGF receptor (VEGFR), using gene therapy techniques that deliver antisense oligonucleotides, use of soluble VEGFR, development of receptor tyrosine kinase (RTK) inhibitors, and monoclonal antibodies (Mab) directed against VEGF [Kim]. The most promising approach appears to be a recombinant humanized version of a murine anti-human VEGF Mab (rhuMab VEGF, Bevacizumab). This Mab has been tested in patients with metastatic cancer [Gordon, Margolin]. There are, however, several disadvantages to the use of antibody therapy. Importantly, passive immunization strategies involve the transfer of antibody to the patient, and immunity is short-lived as the antibodies are cleared from the circulation. Likewise, Mabs are often immunogenic themselves, thereby limiting their long-term use. Also, large antibody volumes are necessary for effective sustained immunization.

The use of vaccines to prevent or treat ovarian cancer is a highly attractive approach because of the expected minimal side effects of vaccine therapy. Many cancers express tumor-associated antigens (TAA) that serve as targets for cancer vaccines. Strategies for immunization have included whole cell vaccines, protein and DNA vaccines, as well as peptide vaccines; each type of antitumor vaccine has its advantages and limitations. Peptides are an attractive anticancer vaccine in that they are safe (free of pathogens and oncogenic potential), stable, easily constructed, and are a cost-effective vaccine system [Dakappagari, Peoples, Kaumaya]. Importantly, peptide vaccines lead to sustained immune responses and memory, unlike that from passive immunization. Limitations of peptide vaccines include the fact that unmodified peptides are rarely immunogenic; thus rational peptide design is imperative to the development of an effective antitumor vaccine.

SUMMARY OF THE INVENTION

The present invention provides new compounds and compositions for stimulating the immune system and for treating malignancies associated with overexpression of the VEGF protein. The compounds are immunogenic epitopes of the human VEGF protein and human EG-VEGF protein, and chimeric and multivalent peptides that comprise such epitopes.

The first group of compounds are referred to hereinafter collectively as "VEGF epitopes". The VEGF epitopes comprise from about 15 to about 50 amino acids, more preferably from 17 to 40 amino acids, most preferably from 18 to 35 amino acids. In one aspect, the VEGF epitope shown in Table 1 below or an antigenic or functional equivalent thereof:

TABLE 1

| Immunogen | Residues | Amino Acid Sequence | Secondary Structure |
|---|---|---|---|
| VEGF | 126-143 (of SEQ ID NO: 1) | KCECRPKKDRARQENPCG | Turn-Helix-Turn |
| EG-VEGF | 50-67 (of SEQ ID NO: 2) | CTPLGREGEECHPGSHKV | Turn-Helix-Turn |

In another aspect the VEGF epitope comprises amino acid 4 through amino acid 21 of human VEGF (as shown below), amino acid 24-38 of human VEGF, amino acid 127 through amino acid 144 of human VEGF, amino acid 102 through amino acid 122 of VEGF, amino acid 162 through amino acid 175 of human VEGF, or amino acid 76 through amino acid 96 of VEGF.

The human VEGF sequence is:

```
  1 MNFLLSWVHWSLALLLYLHHAKWSQAAPMAEGGGQNHHEVVKFMDVYQRSYCHPIETLD
 60 IFQEYPDEIEYIFKPSCVPLMRCGGCSNDEGLECVPTEESNITMQIMRIKPHQGQHIGEM
120 SFLQHNKCECRPKKDRARQENPCGPCSERRKHLFVQDPQTCKCSCKNTHSRCKARQLELN
180 ERTCRCDKPRR 190 (SEQ ID NO: 1)
```

In another aspect, the present VEGF epitope comprises amino acid 5 through amino acid 15 of human EG-VEGF protein (as shown below), amino acid 24 through amino acid 34 of human EG-VEGF, amino acid 50 through amino acid 75 of human EG-VEGF, or amino acid 86 through amino acid 102 of human EG-VEGF.

The human EG-VEGF sequence is:

(SEQ ID NO: 2)
1 MRGATRVSIMLLLVTVSDCAVITGACERDVQCGAGTCCAISLWLRGLRMCTPLGREGEE

CHPGSHKVPFFRKRKHHTCPCLPNLLCSRFPDGRYRCSMDLKNINF105

The present invention also provides chimeric peptides, referred to hereinafter as "chimeric VEGF peptides", which comprise at least one of the present VEGF epitopes or an antigenic or functional equivalent thereof. Preferably the chimeric VEGF peptides are from about 35 to about 150, more preferably from about 35 to about 70 amino acids in length. The chimeric VEGF peptides comprise three units. The first unit comprises at least one VEGF epitope or an antigenic or functional equivalent thereof. The second unit is a helper T (Th) cell epitope, preferably a promiscuous Th cell epitope. As used herein a "promiscuous Th cell epitope" is one that promotes release of cytokines that assist in bypassing MHC restriction. The second unit is from about 14 to about 22, more preferably about 15 to 21, most preferably 16 amino acids in length. Preferably, the Th cell epitope has one of the following amino acid sequences:

```
N-S-V-D-D-A-L-I-N-S-T-I-Y-S-Y-F-P-S-V,
SEQ ID NO. 3, referred to hereinafter as "TT";

P-G-I-N-G-K-A-I-H-L-V-N-N-Q-S-S-E,
SEQ ID NO. 4, referred to hereinafter as "TT1";

Q-Y-I-K-A-N-S-K-F-I-G-I-T-E-L,
SEQ ID NO. 5, referred to hereinafter as "P2";

F-N-N-F-T-V-S-F-W-L-R-V-P-K-V-S-A-S-H-L-E
SEQ ID NO. 6, referred to hereinafter as "P30";

L-S-E-I-K-G-V-I-V-H-R-L-E-G-V,
SEQ ID NO. 7, referred to hereinafter as "MVF";

F-F-L-L-T-R-I-L-T-I-P-Q-S-L-N,
SEQ ID NO. 8, referred to hereinafter as "HBV";

T-C-G-V-G-V-R-V-R-S-R-V-N-A-A-N-K-K-P-E,
SEQ ID NO. 9, referred to hereinafter as "CSP".
```

The third unit of the chimeric peptide joins the first and second peptide units. The third unit is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu, SEQ ID NO. 10.

The present invention also provides multivalent VEGF peptides, which comprise a plurality, i.e., at least two of the present VEGF epitopes or functional equivalents thereof and a Th cell epitope. The VEGF epitopes and Th cell epitope are connected to a core β sheet template. Preferably, the template comprises two strands of alternating leucine and lysine residues, which are connected by a linker. The linker is an amino acid or, preferably, a peptide of from about 2 to about 15 amino acids, more preferably from about 2 to about 10 amino acids, most preferably from about 2 to about 6 amino acids in length. The most preferred linker comprises the amino acid sequence Gly-Pro-Ser-Leu, SEQ ID NO. 10.

The present invention also relates to an immunogenic composition containing a mixture of VEGF epitopes, a chimeric VEGF peptide, or a multivalent VEGF peptide and a pharmacologically acceptable carrier. In one aspect, the carrier is a biodegradeable microsphere. Such immunogenic compositions are useful for treating malignancies with which overexpression of the VEGF protein is associated.

The present invention also relates to polynucleotides which encode at least one of the VEGF epitopes described above. Such polynucleotides are useful for producing the epitope by recombinant techniques. The present invention also relates to isolated polynucleotides having a sequence which encodes a chimeric VEGF cell peptide of the present invention. Such polynucleotides are useful for preparing the chimeric VEGF cell peptide. Such polynucleotides are also useful in an immunogenic composition (e.g., DNA vaccine) for treating or preventing malignancies in which overexpression of the VEGF protein is associated. Preferably, such immunogenic compositions are administered intramuscularly.

DETAILED DESCRIPTION OF THE INVENTION

Figure 1:
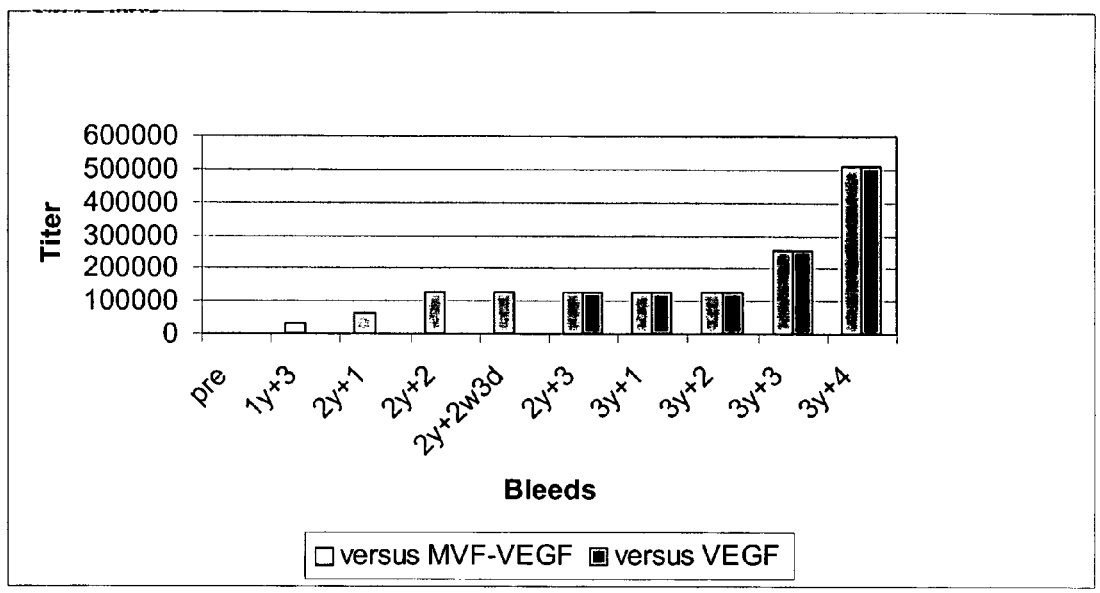
FIG. 1 shows high-titered sera recognizing the B-cell epitope (VEGF) and immunogen (MVF-VEGF) following active immunization with VEGF peptides. ELISA of New Zealand white rabbit sera against VEGF, demonstrating titers >1:500,000 at 4 weeks following the second booster vaccination (3y+4).

The present invention will now be described by reference to more detailed embodiments, with occasional reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Throughout this disclosure, reference will be made to compounds according to the invention. Reference to such compounds, in the specification and claims, includes esters and salts of such compounds. Thus, even if not explicitly recited, such esters and salts are contemplated, and encompassed, by reference to the compounds themselves.

Additionally, as used herein, "peptide," "polypeptide," and "protein," can and will be used interchangeably. "Peptide/polypeptide/protein" may be used to refer to any of the three, but recitations of any of the three contemplate the other two. That is, there is no intended limit on the size of the amino acid polymer (peptide, polypeptide, or protein), that can be expressed using the present invention. Additionally, the recitation of "protein" is intended to encompass enzymes, hormone, receptors, channels, intracellular signaling molecules, and proteins with other functions. Multimeric proteins can also be made in accordance with the present invention.

While the naturally occurring amino acids are discussed throughout this disclosure, non-naturally occurring amino acids, or modified amino acids, are also contemplated and within the scope of the invention. In fact, as used herein, "amino acid" refers to natural amino acids, non-naturally occurring amino acids, and amino acid analogs, all in their D and L stereoisomers. Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodityrosine, and di-isodityrosine are formed post-translationally. Use of natural amino acids, in particular the 20 genetically encoded amino acids, is preferred.

The present invention provides peptides that are immunogenic epitopes of the human VEGF protein and the human EG-VEGF protein, referred to hereinafter collectively as "VEGF epitopes".

The VEGF epitopes and their antigenic equivalents are capable of invoking a humoral response, which results in the production of antibodies that are immunoreactive with the recombinant human VEGF protein and/or human EG-VEGF protein. The VEGF epitopes encompass peptides having one of the sequences, referred to hereinafter as the "reference sequences", as described above. The reference sequences were selected and scored using computer-aided analysis using six correlates of antigenicity: (a) the profiles of chain flexibility and mobility of individual sequences was calculated according to Karplus and Schultz, Naturwiss 72:212-

213, 1985; (b) hydropathy profiles were generated over a seven residue span setting and were finally smoothed with a three residue span using the scale of Kyte and Doolittle, J. Mol. Biol. 157:105-132, 1982; (c) hydrophilicity profiles were generated over a 6-residue window using the program of Hopp and Woods, Proc. Natl. Acad. Sci. USA 78:3824-3828, 1981; (d) analysis of the exposure of an amino acid residue to water using a 1.4 Å probe) was carried out b the solvent exposure algorithm of Rose, Science 229:834-838, 1985; (e) protrusion indices that predicts portions of proteins that are accessible and protrude into the solvent were calculated by the method of Thornton, EMBO J. 5:409-413, 1986; (f) the probability that a five residue sequence is antigenic was determined by the method of Welling, FEBS Lett 188:215-218, 1985. The basic premise is that the algorithms used in the predictions will always locate regions that are surface-exposed on the protein and therefore most likely to be involved in antibody binding.

Sequences were given a score of 1 to 6 based on their respective index values and were ranked: the highest ranking sequences had the highest individual score for the analyses examined (6/6), and successive candidates had the next highest score (5/6), etc. The best scoring epitopes were further ranked by correlation with their secondary structural attributes, e.g., an amphiphilic α-helical sequence or a β-turn loop region are preferred over a random coil fragment. Computer programs by Chou and Fasman, Adv. Enzymol. Relat. Subj. Biochem. 47: 45-148, 1978 were used to predict the secondary structure (α-helix, β-strand/sheet, (3-turn/loop, random coil) and helical amphiphilic moment. Electrostatic ion pairs and helix dipole interaction in helical segment were also considered (e.g., hydrophobic/hydrophilic balance). Preferably, the hydrophilic/hydrophobic balance is from 2/2 to 4/1.

As described herein, the VEGF cell epitopes also encompass peptides that are antigenic and functional equivalents of the peptides described above. Such functional equivalents have an altered sequence in which one or more of the amino acids in the corresponding reference sequence is substituted, or in which one or more amino acids are deleted from or added to the reference sequence. For example, cysteine residues may be deleted or replaced with other amino acids to prevent formation of incorrect intramolecular disulfide bridges upon renaturation.

While it is possible to have nonconservative amino acid substitutions, it is preferred that, except for the substitutions that are made to replace cysteine, the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine and isoleucine, with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, methionine, and glycine, with another.

Preferably, the deletions and additions are located at the amino terminus, the carboxy terminus, or both, of one of the sequences shown above. As a result of the alterations, the VEGF functional epitope equivalent has an amino acid sequence which is at least 70% identical, preferably at least 80% identical, more preferably at least 90% identical, most preferably, at least 95% identical to the corresponding reference sequences. Sequences which are at least 90% identical have no more than 1 alteration, i.e., any combination of deletions, additions or substitutions, per 10 amino acids of the reference sequence. Percent identity is determined by comparing the amino acid sequence of the variant with the reference sequence using MEGALIGN project in the DNA STAR program.

For functional equivalents that are longer than a corresponding reference sequence, it is preferred that the functional equivalent have a sequence which is at least 90% identical to the reference sequence and the sequences which flank the reference sequence in the wild-type VEGF or EG-VEGF protein. In addition to being an antigenic equivalent of the naturally-occurring human VEGF epitope, the functional equivalent is also capable of raising antibodies that disrupt bind of human VEGF or EG-VEGF to the VEGF receptor.

Preparation of Epitopes and Co-Linear Chimeric Peptides

The VEGF epitopes, chimeric VEGF peptides, and multivalent VEGF peptides, preferably, are synthesized using commercially available peptide synthesizers. Preferably, the chemical methods described in Kaumaya et al., "DE NOVO" ENGINEERING OF PEPTIDE IMMUNOGENIC AND ANTIGENIC DETERMINANTS AS POTENTIAL VACCINES, in Peptides, Design, Synthesis and Biological Activity (1994), pp 133-164, which is specifically incorporated herein by reference, are used.

The VEGF epitopes and chimeric peptides may also be produced using cell-free translation systems and RNA molecules derived from DNA constructs that encode the epitope or peptide. Alternatively, the VEGF epitopes or chimeric peptides are made by transfecting host cells with expression vectors that comprise a DNA sequence that encodes the respective epitope or chimeric peptide and then inducing expression of the polypeptide in the host cells. For recombinant production, recombinant constructs comprising one or more of the sequences which encode the epitope, chimeric peptide, or a variant thereof are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

The VEGF epitopes and chimeric peptides may be expressed in suitable host cells, such as for example, mammalian cells, yeast, bacteria, insect cells or other cells under the control of appropriate promoters using conventional techniques. Suitable hosts include, but are not limited to, *E. coli*, *P. pastoris*, Cos cells and 293 HEK cells. Following transformation of the suitable host strain and growth of the host strain to an appropriate cell density, the cells are harvested by centrifugation, disrupted by physical or chemical means, and the resulting crude extract retained for further purification of the epitope or chimeric peptide.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, and high performance liquid chromatography (HPLC), and affinity chromatography may be used to isolate the recombinant polypeptide. To produce glycosylated epitopes and chimeric peptides, it is preferred that recombinant techniques be used. To produce glycosylated epitopes and chimeric peptides which contain the same, it is preferred that mammalian cells such as, Cos-7 and Hep-G2 cells be employed in the recombinant techniques.

Naturally occurring variants of the VEGF epitopes above may also be isolated by, for example, by screening an appropriate cDNA or genomic library with a DNA sequence encoding the polypeptide.

Identifying Functional Equivalents of the VEGF Peptide

Functional equivalents of the VEGF epitopes shown above may generally be identified by modifying the sequence of the epitope and then assaying the resulting polypeptide for the ability to stimulate an immune response, e.g., production of antibodies. For example, such assays may generally be performed by preparing a chimeric peptide which comprises the modified polypeptide and a promiscuous Th cell epitope, injecting the chimeric peptide into a test animal and assaying for antibodies. Such antibodies may be found in a variety of body fluids including sera and ascites. Briefly, a body fluid sample is isolated from a warm-blooded animal, such as a human, for whom it is desired to determine whether antibodies specific for the human VEGF are present. The body fluid is incubated with the human VEGF or EG-VEGF protein under conditions and for a time sufficient to permit immunocomplexes to form between the polypeptide and antibodies specific for the protein and then assayed, preferably using an ELISA technique. In such technique, the colorimetric change is measured at 490 nm. Epitopes which induce production of antibodies that exhibit a titer equal to 10,000 or greater for human VEGF or EG-VEGF protein, are preferred. As used herein a titer of 10,000 refers to an absorbance value of 0.2 above background.

Functional equivalents of the VEGF epitope are further identified by determining whether the peptide can be used to raise antibodies that disrupt binding of human VEGF to the human VEGF receptor as described in Example 1 below.

Determining Optimum Dosages for Inhibiting Agiogenesis or Treating Cancer

In vivo methods can also be used to characterize functional equivalents of the present epitopes or to determine optimum dosages of the VEGF chimeric and multivalent peptides. In one aspect, a xenograft model can be used. In this model, subcutaneous tumors are established with an ovarian cancer (SKOV3) cell line by injecting BALB/c athymic nude mice in the right flank with $2\times10^6$ tumor cells mixed with matrigel. Tumors are allowed to reach 150-200 $mm^3$, and then mice randomized to receive either intraperitoneal injection of anti-VEGF or anti-EG-VEGF antibodies or nonspecific IgG antibodies (control) every 3 days. Tumor volumes are measured and calculated twice weekly. Tumor permeability is assessed using the Miles assay, in which treated and control mice undergo intracardiac injection with Evans blue solution. The animals are then be sacrificed, photographed, and the amount of permeability compared between treated and control mice. The matrigel plug is removed, and vessel density examined by CD31 immunohistochemistry.

Active immunization with the VEGF and EG-VEGF peptide vaccines is then investigated in vivo. Previous investigation has shown that the introduction of SKOV3 ovarian cancer cells ($10\times10^6$ cells in 200 μL PBS) in the peritoneal cavity of female immunodeficient mice (BALB/c nu/nu) leads to a clinical condition identical to that seen with women with advanced ovarian cancer, including the establishment of tumors coating the surface of intraperitoneal organs, as well as the development of large-volume ascites within 4 weeks of inoculation [9]. Likewise, subcutaneous injection of SKOV3 cells ($10\times10^6$ cells in 50 μL PBS) leads to measurable tumor within 10 days of inoculation. As such, a combination of both subcutaneous and intraperitoneal injection of SKOV3 cells can be investigated in determining the in vivo efficacy of peptide immunization against ovarian tumors.

Groups of 10 mice are vaccinated with the VEGF and EG-VEGF epitopes three times at 3-week intervals. Antibody titers are monitored by ELISA. Three weeks following the third vaccination, mice are challenged with SKOV3 cells. Subcutaneous tumors are measured weekly using calipers, and tumor volumes are estimated based on the assumption that tumors are spherical. Because intraperitoneal tumor growth and distribution cannot be measured directly, mice are killed by anesthetic overdose approximately 4 weeks following inoculation and location of tumor, presence of ascites, and tumor location and size recorded.

Further evidence of the anti-angiogenic effect of the elicited anti-VEGF antibodies is suggested by inhibition of ovulation by antibody following stimulation by gonadotropins. Because ovulation is regulated through angiogenic stimuli [18], it is believed that anti-angiogenic efficacy of the anti-peptide antibodies would lead to disruption of ovulation. In this experiment, groups of 24 day old female Sprague-Dawley rats are immunized with anti-peptide antibodies against VEGF, EG-VEGF, both VEGF and EG-VEGF, or nonspecific antibody (control). Four hours following immunization, the rats are treated with 20 IU pregnant mares' serum gonadotropin (PMSG) and 24-hours later with 20 IU human chorionic gonadotropin (hCG), the hormonal stimulatory sequence that leads to ovulation. After 5 days, the rats are killed and an assessment of the efficacy of inhibition of ovulation will be made. It is believed that in rats treated with anti-peptide antibodies, ovulation will be efficiently inhibited and a decreased ovarian weight and alterations in the estrous cycle and decreased follicular growth and decreased CD31 immunostaining will be seen compared with control animals.

Further assessment of the in vivo activity of VEGF peptide vaccines can be conducted in a transgenic mouse model that expresses human VEGF under the control of the rat insulin promoter (Rip1 VEGF-A) [20]. In this model, overexpression of VEGF was shown to accelerate the onset of tumor angiogenesis, and spontaneous tumors were shown to develop within 10 weeks (single-transgenic mouse, RIP1Tag2) and 14 weeks (double-transgenic mouse, Rip1Tag2/Rip1 VEGF-A). In this studies, mice are immunized with VEGF or EG-VEGF epitopes on a compressed schedule to match the transgenic mouse tumor development (initial immunization will be at 5 weeks, with subsequent booster at 7 and 9 weeks). Mice are then sacrificed, and tumor volumes calculated. Tumors are fixed, embedded in OCT, snap frozen, and analyzed by H&E staining. Vessel density can determined by CD31 immunostaining. It is expected that VEGF peptide vaccination will lead to the prevention or inhibition of tumor formation in this transgenic mouse model overexpressing VEGF, and that surrogates for angiogenesis will be decreased.

Polynucleotides

The present invention also provides isolated polynucleotides which encode the VEGF epitopes and the chimeric peptides of the present invention. The present polynucleotides also encompass polynucleotides having sequences that are capable of hybridizing to the nucleotide sequences of under stringent conditions, preferably highly stringent conditions. Hybridization conditions are based on the melting temperature (Tm) of the nucleic acid binding complex or probe, as described in Berger and Kimmel (1987) Guide to Molecular Cloning Techniques, Methods in Enzymology, vol 152, Academic Press. The term "stringent conditions, as used herein, is the "stringency" which occurs within a range from about Tm-5 (5° below the melting temperature of the probe) to about 20° C. below Tm. As used herein "highly stringent"

conditions employ at least 0.2×SSC buffer and at least 65° C. As recognized in the art, stringency conditions can be attained by varying a number of factors such as the length and nature, i.e., DNA or RNA, of the probe; the length and nature of the target sequence, the concentration of the salts and other components, such as formamide, dextran sulfate, and polyethylene glycol, of the hybridization solution. All of these factors may be varied to generate conditions of stringency which are equivalent to the conditions listed above.

Polynucleotides comprising sequences encoding a VEGF epitope or a chimeric peptide of the present invention may be synthesized in whole or in part using chemical methods or, preferably, recombinant methods which are known in the art. Polynucleotides which encode a VEGF may be obtained by screening a genomic library or cDNA library with antibodies immunospecific for the to identify clones containing such polynucleotide.

The polynucleotides are useful for producing a VEGF B epitope. chimeric peptide, or multivalent peptide. For example, an RNA molecule encoding a chimeric peptide is used in a cell-free translation systems to prepare such polypeptide. Alternatively, a DNA molecule encoding a VEGF epitope or a chimeric peptide is introduced into an expression vector and used to transform cells. Suitable expression vectors include for example chromosomal, non-chromosomal and synthetic DNA sequences, e.g., derivatives of SV40, bacterial plasmids, phage DNAs; yeast plasmids, vectors derived from combinations of plasmids and phage DNAs, viral DNA such as vaccinia, adenovirus, fowl pox virus, pseudorabies, baculovirus, and retrovirus. The DNA sequence is introduced into the expression vector by conventional procedures.

Accordingly, the present invention also relates to recombinant constructs comprising one or more of the present polynucleotide sequences. Suitable constructs include, for example, vectors, such as a plasmid, phagemid, or viral vector, into which a sequence that encodes VEGF epitope or the chimeric peptide has been inserted. In the expression vector, the DNA sequence which encodes the epitope or chimeric peptide is operatively linked to an expression control sequence, i.e., a promoter, which directs mRNA synthesis. Representative examples of such promoters, include the LTR or SV40 promoter, the *E. coli* lac or trp, the phage lambda PL promoter and other promoters known to control expression of genes in prokaryotic or eukaryotic cells or in viruses. The expression vector, preferably, also contains a ribosome binding site for translation initiation and a transcription terminator. Preferably, the recombinant expression vectors also include an origin of replication and a selectable marker, such as for example, the ampicillin resistance gene of *E. coli* to permit selection of transformed cells, i.e., cells that are expressing the heterologous DNA sequences. The polynucleotide sequence encoding the VEGF epitope or the chimeric peptide is incorporated into the vector in frame with translation initiation and termination sequences. Preferably, the polynucleotide further encodes a signal sequence which is operatively linked to the amino terminus of the VEGF epitope, or chimeric peptide.

The polynucleotides encoding the VEGFF or EG-VEGF epitope or the chimeric peptides comprising such epitopes are used to express recombinant peptide using techniques well known in the art. Such techniques are described in Sambrook, J. et al (1989) Molecular Cloning A Laboratory Manual, Cold Spring Harbor Press, Plainview, N.Y. and Ausubel, F. M. et al. (1989) Cuurent Protocols in Molecular Biology, John Wile & Sons, New York, N.Y. Polynucleotides encoding the VEGF or EG-VEGF epitope or the chimeric peptides comprising such epitopes are also used to immunize animals.

Pharmaceutical Compositions

Pharmaceutical compositions which comprise mixtures of VEGF and/or EG-VEGF epitopes, chimeric VEGF or EG-VEGF peptides, and multivalent VEGF- or EG-VEGF peptides or the polynucleotides which encode the same are preferably formulated for use as a pharmaceutical composition (e.g., an immunogenic composition or a vaccine). Such compositions generally comprise one or more of the present VEGF and/or EG-VEGF epitopes, one or more of the present VEGF and/or EG-VEGF chimeric peptides, or one or more the present VEGF or EG-VEGF multivalent peptides or the polynucleotides which encode the same in combination with a pharmaceutically acceptable carrier, excipient, or diluent. Such carriers will be nontoxic to recipients at the dosages and concentrations employed.

In addition to the epitopes, multivalent peptides, and chimeric peptides (which functions as antigens) or the polynucleotide which encodes the same, other components, such as a vehicle for antigen delivery and immunostimulatory substances designed to enhance the protein's immunogenicity, are, preferably, included in the pharmaceutical composition. Examples of vehicles for antigen delivery include aluminum salts, water-in-oil emulsions, biodegradable oil vehicles, oil-in-water emulsions, biodegradable microcapsules, and liposomes. For the vaccines that comprise the chimeric peptide, one potential vehicle for antigen delivery is a biodegradable microsphere, which preferably is comprised of poly(D, L-lactide-co-glycolide) (PLGA).

While any suitable carrier known to those of ordinary skill in the art may be employed in the pharmaceutical compositions of this invention, the type of carrier will vary depending on the mode of administration and whether a substantial release is desired. For parenteral administration, such as subcutaneous injection, the carrier preferably comprises water, saline, alcohol, a fat, a wax, or a buffer. Biodegradable microspheres (e.g., polylactic galactide) may also be employed as carriers for the pharmaceutical compositions of this invention. Optionally, the pharmaceutical composition comprises an adjuvant.

The VEGF epitope mixtures, chimeric and multivalent peptides and the polynucleotides which encode the same are useful for enhancing or eliciting, in a subject or a cell line, a humoral response and, preferably, a cellular immune response (e.g., the generation of antigen-specific cytolytic T cells). As used herein, the term "subject" refers to any warm-blooded animal, preferably a human. A subject may be afflicted with cancer, such as ovarian cancer, or may be normal (i.e., free of detectable disease and infection). The pharmaceutical composition is particularly useful for treating women who have a family history of ovarian cancer or who have been diagnosed as having ovarian cancer.

Methods of Treatment

The present invention also provides methods of treating a cancer which is associated with overexpression of VEGF By "treating" is meant inhibiting or slowing or retarding the growth of the tumor. Such cancers include ovarian cancer. The method comprises administering a pharmaceutical composition comprising a VEGF and/or EG-VEGF epitope mixture, one or more VEGF chimeric peptides or one or more VEGF multivalent peptides of the present invention to a subject. Preferably multiple intramuscular injections, at three week intervals are used to administer the pharmaceutical composition.

The present invention also provides methods of inhibiting angiogenesis in rapidly growing tissues in a subject. The methods comprise administering a mixture of VEGF and/or EG-VEGF epitopes of the present invention, one or more chimeric VEGF and/or EG-VEGF chimeric peptides of the present invention, one or more multivalent VEGF and/or EG-VEGF polypeptides of the present invention or polynucleotides that encode the same to the subject.

The peptides of this invention relate to the representative peptides as described above, and to antigenically related variants of these peptides. "Antigenically related variants" can be either natural variants or artificially modified variants that immunologically mimic the VEGF or EG-VEGF epitope described above. Such artificially modified variants can be made by synthetic chemistry of recombinant DNA mutagenesis techniques that are well known to persons skilled in the art (see for example Chapter 15 of Sambrook, et al. "Molecular Cloning a Laboratory Manual" (1989) Cold Spring Harbor Laboratory Press). The antigenically related variants of the peptides should have an amino acid sequence identity of at least 75% to one of the VEGF or EG-VEGF epitopes described above (and more preferably at least 85%, and most preferably at least 95% identity), whilst still being capable of immunologically mimicking the corresponding antigenic determinant site of the human VEGF or EG-VEGF protein.

For this invention "immunologically mimicking the corresponding antigenic determinant site of the VEGF or EG-VEGF protein is defined as a (variant) peptide being capable of inducing antibodies that specifically recognize one of the wild-type epitope sequences described above in the context of the whole VEGF or EG-VEGF protein AND/OR defined as a (variant) peptide being capable of being recognized by the same immunospecific antibody that recognizes one of the VEGF or EG-VEGF epitopes described above in the context of the whole VEGF or EG-VEGF protein. In the first definition, the variant peptide should be capable of inducing such antibodies either by itself, or in conjunction with a carrier molecule. In the second definition, the variant peptide should be capable of being recognized either by itself, or in conjunction with a carrier molecule. Antigenically related variants may have had amino acids added, inserted, substituted or deleted. Preferred variants are those that differ from the referents by conservative (preferably single) amino acid substitutions.

Polypeptides of the present invention can be prepared in any suitable manner. Such polypeptides include recombinantly produced polypeptides, synthetically produced polypeptides, or polypeptides produced by a combination of these methods. Means for preparing such polypeptides are well understood in the art, however examples of the method are presented in the Examples section.

Polynucleotides of the Invention

The polynucleotides of the invention also relates to DNA sequences that can be derived from the amino acid sequences of the peptides and polypeptides of the invention bearing in mind the degeneracy of codon usage. This is well known in the art, as is knowledge of codon usage in different expression hosts which is helpful in optimizing the recombinant expression of the peptides and polypeptides of the invention.

The invention also provides polynucleotides which are complementary to all the above described polynucleotides.

When the polynucleotides of the invention are used for the recombinant production of polypeptides of the present invention, the polynucleotide may include the coding sequence for the polypeptide, by itself; or the coding sequence for the polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci* USA (1989) 86:821-824, or is an HA tag, or is glutathione-s-transferase. The polynucleotide may also contain non-coding 5' and 3' sequences, such as transcribed, non-translated sequences, splicing and polyadenylation signals, ribosome binding sites and sequences that stabilize mRNA.

Vectors, Host Cells, Expression

The present invention also relates to vectors which comprise a polynucleotide or polynucleotides of the present invention, and host cells which are genetically engineered with vectors of the invention and to the production of peptides or polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transfection, microinjection, cationic lipid-mediated transfection, electroporation, transduction, scrape loading, ballistic introduction or infection.

Representative examples of appropriate hosts include bacterial cells, such as meningococci, streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well known and routine techniques, such as, for example, those set forth in Sambrook et al., MOLECULAR CLONING, A LABORATORY MANUAL (supra).

For secretion of the translated protein into the lumen of the endoplasmic, reticulum, into the periplasmic space or into the extracellular environment, appropriate secretion signals may be incorporated into the desired polypeptide. These signals may be endogenous to the polypeptide or they may be heterologous signals.

Purification of Recombinantly Expressed Peptides/Polypeptides

Peptides and polypeptides of the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxyapatite chromatography and lectin chromatography. Most preferably, high performance liquid chromatography is employed for purification. Well known techniques for refolding proteins may be employed to regenerate active conformation when the polypeptide is denatured during isolation and or purification.

Although the gene sequence of the chimeric VEGF polypeptide in the vector can be tagged with a Histidine-tag sequence which aids the purification of the polypeptide, it is not an essential element to the invention, as polypeptides without the Histidine-tag can still be purified by one of the techniques mentioned above.

Antibodies

The peptides and polypeptides of the invention, or cells expressing them can also be used as immunogens to produce antibodies immunospecific for the wild-type VEGF or EG-VEGF. The term "immunospecific" means that the antibodies have substantially greater affinity for the peptides or polypeptides of the invention than their affinity for other related polypeptides in the prior art.

Antibodies generated against the peptides or polypeptides can be obtained by administering it to an animal, preferably a nonhuman, using routine protocols in the immunization of an animal with an antigen, the collection of the blood, the isolation of the serum and the use of the antibodies that react with the peptide. The serum or IgG fraction containing the antibodies may be used in analyzing the protein. For preparation of monoclonal antibodies, any technique which provides antibodies produced by continuous cell line cultures can be used. Examples include the hybridoma technique (Kohler, G. and Milstein, C., Nature (1975) 256:495-497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77-96, Alan R. Liss, Inc., 1985).

Techniques for the production of single chain antibodies (U.S. Pat. No. 4,946,778) can also be adapted to produce single chain antibodies to peptides or polypeptides of this invention. Also, transgenic mice, or other organisms including other mammals, may be used to express humanized antibodies.

The above-described antibodies may be employed to isolate or to identify clones expressing the peptide or to purify the peptides or polypeptides of the invention by affinity chromatography.

Vaccines

Another aspect of the invention is a vaccine composition comprising an immunogenic amount of at least one peptide or polypeptide of the invention. Preferably the composition should also comprise a pharmaceutically acceptable excipient. Vaccine preparation is generally described in Vaccine Design ("The subunit and adjuvant approach" (eds. Powell M. F. & Newman M J). (1995) Plenum Press New York).

Additionally, the peptides and polypeptides of the present invention are preferably adjuvanted in the vaccine formulation of the invention. Suitable adjuvants include an aluminum salt such as aluminum hydroxide gel (alum) or aluminum phosphate, but may also be a salt of calcium, iron or zinc, or may be an insoluble suspension of acylated tyrosine, or acylated sugars, cationically or anionically derivatized polysaccharides, or polyphosphazenes. Other known adjuvants include CpG containing oligonucleotides. The oligonucleotides are characterized in that the CpG dinucleotide is unmethylated. Such oligonucleotides are well known and are described in, for example WO96/02555.

Further preferred adjuvants are those which induce an immune response preferentially of the TH1 type. High levels of Th1-type cytokines tend to favor the induction of cell mediated immune responses to the given antigen, whilst high levels of Th2-type cytokines tend to favor the induction of humoral immune responses to the antigen. Suitable adjuvant systems include, for example monophosphoryl lipid A, preferably 3-de-O-acylated monophosphoryl lipid A (3D-MPL), or a combination of 3DMPL together with an aluminum salt. CpG oligonucleotides also preferentially induce a TH1 response. An enhanced system involves the combination of a monophosphoryl lipid A and a saponin derivative particularly the combination of QS21 and 313-MPL as disclosed in WO 94/00153, or a less reactogenic composition where the QS21 is quenched with cholesterol as disclosed in WO 96/33739. A particularly potent adjuvant formulation involving QS21 3D-MPL & tocopherol in an oil in water emulsion is described in WO 95/17210 and is a preferred formulation.

Another aspect of the invention relates to a method for inducing an immunological response in a mammal which comprises inoculating the mammal with a peptide or polypeptide of the invention adequate to produce antibody to inhibit angiogenesis and to inhibit growth of tumors among others. Yet another aspect of the invention relates to a method of inducing immunological response in a mammal which comprises, delivering a peptide or polypeptide of the invention via a vector directing expression of a polynucleotide of the invention in vivo in order to induce such an immunological response to produce antibody to protect said animal from diseases.

A further aspect of the invention relates to an immunological/vaccine formulation (composition) which, when introduced into a mammalian host, induces an immunological response in that mammal to VEGF or EG-VEGF peptide wherein the composition comprises a polynucleotide encoding a VEGF or EG-VEGF epitope or the VEGF or EG-VEGF epitope itself. The vaccine formulation may further comprise a suitable carrier. The VEGF vaccine composition is preferably administered orally, intranasally or parenterally (including subcutaneous, intramuscular, intravenous, intradermal, transdermal injection). Formulations suitable for parenteral administration include aqueous and non-aqueous sterile injection solutions which may contain anti-oxidants, buffers, bacteriostats, and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant as described above. The dosage will depend on the specific activity of the vaccine and can be readily determined by routine experimentation.

Yet another aspect relates to an immunological/vaccine formulation which comprises the polynucleotide of the invention. Such techniques are known in the art, see for example Wolff et al., Science, (1990) 247: 1465-8.

EXAMPLES

Exemplary methods are described below, although methods and materials similar or equivalent to those described herein can be used in the practice or testing of the present peptides, compositions and methods. All publications and other references mentioned herein are incorporated by reference in their entirety. The materials, methods, and examples are illustrative only and not intended to be limiting.

Example 1

Abstract

VEGF epitopes were identified using a computer-aided analysis employing specific correlates for antigenicity. These epitopes were synthesized, purified, and combined the measles virus fusion (MVF) protein, a T-cell epitope. VEGF peptide antibodies were elicited in mice and rabbits following primary and booster vaccination. ELISA and Western blotting determined antibody specificity. VEGF peptide antibody function was assessed by Fluorokine® VEGF receptor interaction assay. Vascular invasion, a marker of angiogenesis, was determined by injecting C57BL/6 mice subcutaneously with Matrigel™ (a mouse sarcoma-derived basement membrane) incubated with and without recombinant human VEGF protein in the presence or absence of VEGF peptide antibodies and mouse VEGF monoclonal antibodies. Angiogenesis into the Matrigel™ assessed with Hoechst staining, and angiogenesis was determined quantitatively by counting blood vessels that invaded into the Matrigel™ Differences in relative angiogenesis were compared with Student's t-test.

VEGF peptides from the predicted antigenic region elicited high-titer antibodies in mice and rabbits (1:500,000 at 3y+4). These antibodies were demonstrated to be specific for rhVEGF by ELISA and Western blot analysis. In vitro, the VEGF peptide antibodies led to a significant disruption of the normal interaction between VEGF and the VEGF receptor compared with control by the Fluorokine® assay. In vivo, the Matrigel™ invasion assay revealed that VEGF peptide antibodies led to a profound quantitative decrease in blood vessel invasion into the matrix compared with control (vascular invasion of VEGF alone=118.2 versus VEGF+VEGF peptide antibodies=26.4, P=0.005).

Conclusion: VEGF peptide antibodies elicited from antigenic regions of VEGF are immunogenic, specific, and anti-angiogenic. Thus, active immunization with a VEGF peptide vaccine is expected to be a biologically relevant treatment in women with epithelial ovarian cancer.

Materials and Methods

VEGF Epitope Selection

The selection of candidate VEGF B-cell epitopes was performed using computer-aided analysis using specific correlates for antigenicity (Peptide Companion, PeptiSearch), employing the profiles of chain flexibility and motility, hydropathy, protrusion indices, and antigenicity [Kaumaya 1994]. Sequences were given a score of 1 to 6 based on their respective index values and were ranked. The best scoring epitopes were further ranked by correlation with their secondary structural attributes, where an amphiphilic alpha-helical sequence or a beta-turn loop is preferred over random coil fragments. Finally, consideration was given to the individual amino acid sequence. Electrostatic ion pairs and helix dipole interaction in helical segment were also considered (hydrophobic/hydrophilic balance). The sequences receiving the highest scores were selected for further investigation. Our group has evaluated a number of antigenic peptides containing T-cell epitopes derived from non-human sources that have been identified to be "promiscuous" in their recognition in association with many MHC molecules and their capacity to elicit $T_H$ responses [Kaumaya 1993]. Measles virus fusion (MVF) protein sequence 288-302 was chosen as the promiscuous epitope to overcome the challenge of tolerance and MHC polymorphism. The MVF epitope was linearly joined to the VEGF epitope by a four-residue linker (GPSL) on a peptide synthesizer. The glycine and proline residues in the linker potentiate a beta-turn in the oligopeptide, whereas the serine favors hydrogen bonds with the free HN of the backbone. The flexible nature of the linker allows for independent folding of the T- and B-cell epitopes. Peptides were purified by reverse-phase HPLC to ensure >95% purity. The identity of the peptides was performed by matrix-assisted LASER desorption ionization-time of flight spectrometry (MALDI-TOF).

Vaccination and Elicitation of VEGF Peptide Antibodies

To generate VEGF antibodies, New Zealand white rabbits (Charles River Laboratories, Inc., Wilmington, Mass.) and BALB/c mice (Harlan, Indianapolis, Ind.) were immunized subcutaneously at multiple sites with a total of 1 mg of each peptide emulsified in a Squaline/Arlacel vehicle containing nor-MDP (N-acetyl-glucosamine-3 yl-acetyl L-alanyl-D-isoglutamine). Subsequent booster injections were given at 3 weeks (secondary immunization, 2y) and 6 weeks (tertiary immunization, 3y) after primary (1y) immunization. Rabbit and mouse sera were collected weekly, and complement was inactivated by heating to 56° C. High-titered sera were purified on a protein A/G-agarose column (Pierce, Rockford, Ill.), and eluted antibodies were concentrated and exchanged in PBS using Mr 100,000 cutoff centrifuge filter units (Millipore, Bedford, Mass.). Antibody concentration was quantified by ELISA.

Characterization of VEGF Peptide Antibodies

Western blot analysis was undertaken to determine whether the VEGF peptide antibodies recognize the VEGF protein. Proteins, including rhVEGF, were resolved by 15% SDS-PAGE, transferred to nitrocellulose, and probed with VEGF peptide antibodies or a mouse VEGF monoclonal antibody (Ab-4, Neoprobe, Inc., Fremont, Calif.). Protein transfer was monitored with prestained molecular weight standards. Immunoreactive bands were detected by enhanced chemiluminescence (Pierce Biotechnology, Inc., Rockford, Ill.) using horseradish peroxidase-conjugated goat anti-rabbit immunoglobulins.

In an effort to determine the effect of our VEGF peptide antibodies on the interaction of VEGF with the VEGF receptor, we employed the Fluorokine® assay (R&D Systems, Minneapolis, Minn.). In brief, $5\times10^5$ HUVECs were washed and incubated with the biotinylated rhVEGF that in turn binds to the cells via the VEGFR. The cells are then directly incubated with avidin-fluorescein, which attaches to the receptor-bound biotinylated VEGF. Unbound biotinylated cytokine participates in an amplification reaction with the bound cytokine that results in an enhanced signal without compromising specificity. Cells expressing the VEGFR are fluorescently stained, with the intensity of staining proportional to the density of the receptors. Relative receptor density is then determined by flow cytometry. Through this experiment, we initially standardized the flow cytometry component of the assay, in which different cell populations were identified using the supplied positive (rhVEGF) and negative (no stimulation) controls, as well as with an inhibitory antibody provided with the kit. Following standardization, various concentrations of mouse or rabbit VEGF peptide antibodies were used instead of the supplied inhibitory antibody to determine the proportional VEGFR density.

Determination of Anti-Angiogenic Properties of VEGF Peptide Antibodies

Analysis of blood vessel invasion was determined in a mouse model employing Matrigel™, a solubilized basement membrane matrix extracted from EHS mouse sarcoma

[Passiniti]. Matrigel™ is a liquid at 4° C., but polymerizes at 4° C., thus allowing for its removal from an animal host for analysis. Sets of 5 female C57BL/6 mice (Harlan, Indianapolis, Ind.) were injected subcutaneously with a total volume of 500 μL including Matrigel™, various concentrations of rhVEGF, and various concentrations of antibody (either VEGF monoclonal antibody (MAB293, R&D Systems, Minneapolis, Minn.) or VEGF peptide antibodies). After 10 days, the mice were sacrificed. The Matrigel™ plugs were then removed, sectioned, and stained with hematoxylin and eosin and the nuclear stain Hoechst 33342. Invasion into the plug was determined using an inverted fluorescent microscope at 40× magnification. Blood vessels at the periphery of the plug were identified and counted in a circumferential manner around the plug, and counted using computer-aided analysis in a blinded fashion. Statistical comparisons between groups were made using the Student's t-test.

Results

Computer-aided analysis of candidate B-cell epitopes of VEGF was used to select residues 126-1434 of SEQ ID NO: 1 (KCECRPKKDRARQENPCG), which correlates with a secondary structure of turn-helix-turn, as being potentially immunogenic and antigenic. This epitope was linearly joined to the promiscuous T-cell epitope of the measles virus protein (MVF) with the four-residue GPSL linker on a peptide synthesizer. Peptides were purified, and their identity confirmed by MALDI-TOF. Rabbits and mice were immunized subcutaneously with the MVF-VEGF immunogen, and sera was obtained and purified. High VEGF peptide antibody titers (1:500,000 at 4 weeks following tertiary immunization, 3y+4) were identified by ELISA as demonstrated in rabbits in FIG. 1.

Figure 2:
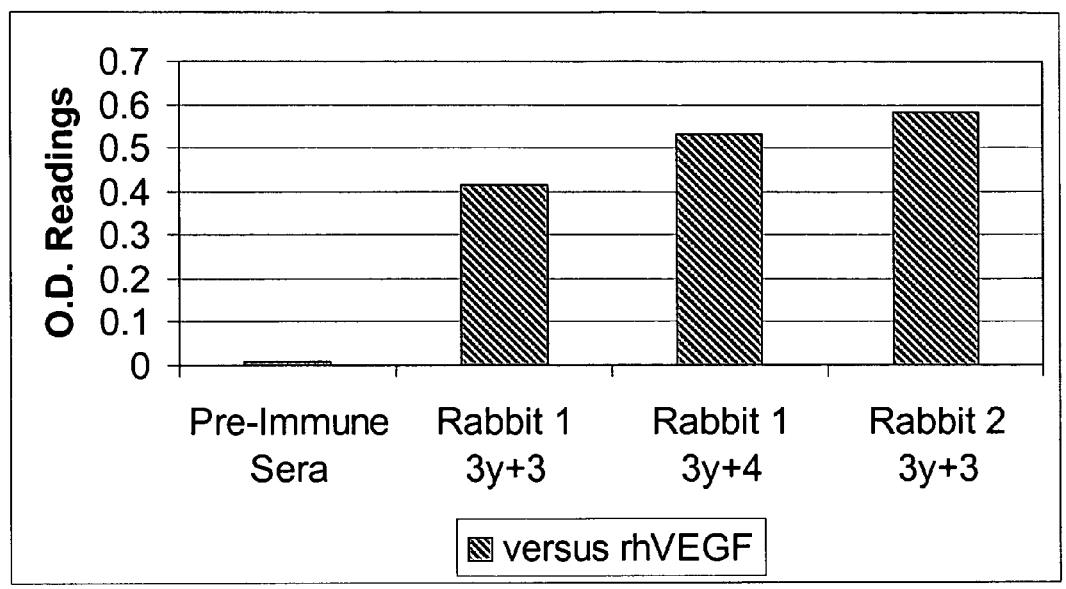
FIG. 2 shows that VEGF peptide antibodies recognize rhVEGF by ELISA. Comparison of rabbit pre-immune sera, prior to vaccination (bar 1) and sera from rabbits vaccinated with VEGF peptides (bars 2-4). Bar 2 and 3 represent rabbit 1 at 3 and 4 weeks after the second booster vaccination (3y+3 and 3y+4, respectively). Bar 4 represents sera from rabbit 2 at a similar bleed.
Figure 3:
FIG. 3 shows a Western blot of rhVEGF blotted with (A) VEGF peptide antibody or (B) Ab-4, a VEGF monoclonal antibody, demonstrating recognition of the appropriate recombinant protein dimer at 42 kDa.
Figure 3:
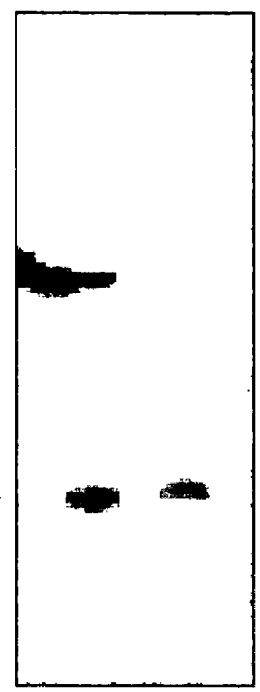

ELISA (FIG. 2) and Western blot (FIG. 3A) demonstrate that VEGF peptide antibodies recognize the rhVEGF protein. Ab-4, a monoclonal antibody against VEGF, was used as a positive control in the Western blot, and confirmed the expected rhVEGF protein homodimer at 42 kDa (FIG. 3B).

Figure 4:
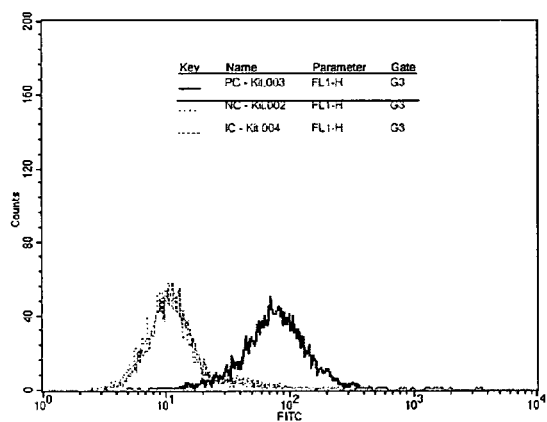
FIG. 4 shows that VEGF peptide antibodies disrupt the normal VEGF-VEGFR interaction by flow cytometry using HUVECs, presumably through depletion of VEGF. (A) Evaluation of the positive (PC), negative (NC) and inhibitor antibody (IC) controls of Fluorokine® assay, and (B) the same PC and NC as in (A), and employing either mouse or rabbit VEGF peptide antibodies, both demonstrating disruption of the normal VEGF-VEGFR interaction. The rabbit antibody labeled as "combo" represents rabbit VEGF peptide antibodies following immunization with both the MVF-VEGF immunogen as well as another immunogen not described in this investigation.
Figure 4:
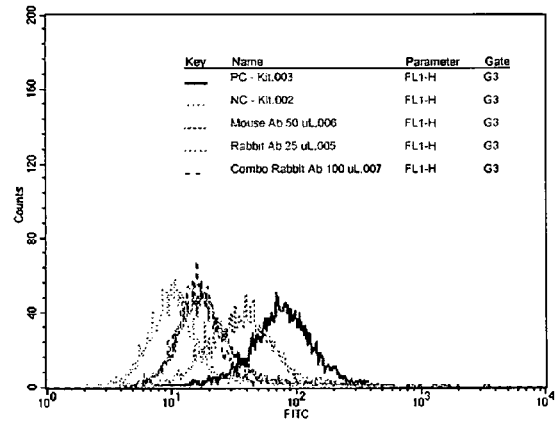

Following demonstration of the antigenic and immunogenic properties of the VEGF peptide antibodies, the functional properties of the antibodies were evaluated. These VEGF peptide antibodies were demonstrated to significantly disrupt the normal interaction between VEGF and the VEGF receptor (VEGFR) as determined by the Fluorokine® assay (FIG. 4). In this experiment, the addition of the VEGF peptide antibodies leads to binding of VEGF, thus leading to a decrease in the normal VEGF-VEGFR interaction.

Figure 5:
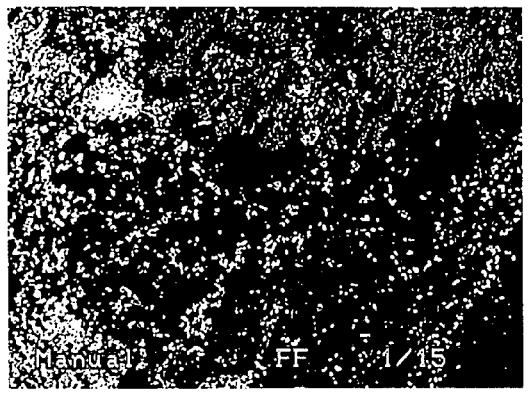
FIG. 5 shows that VEGF peptide antibodies disrupt angiogenesis into Matrigel™. C57BL/6 mice were subcutaneously injected with Matrigel™ incubated with rhVEGF with (FIG. 5A) or without (FIG. 5B) VEGF antibodies. After 10 days, the plugs were removed, stained, and blood vessel invasion was counted. Compared with PBS control, addition of VEGF peptide antibodies significantly disrupts angiogenesis in vivo. Magnification 40×, stained with Hoechst 33342.
Figure 5:
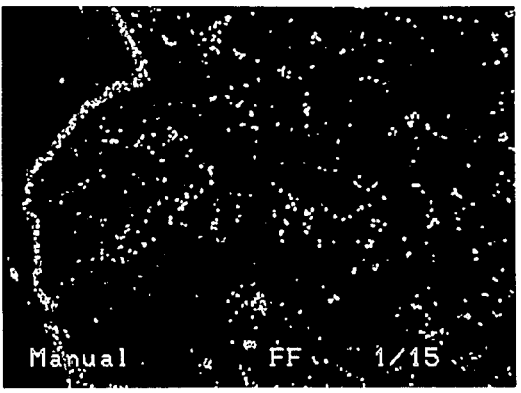
Figure 6:
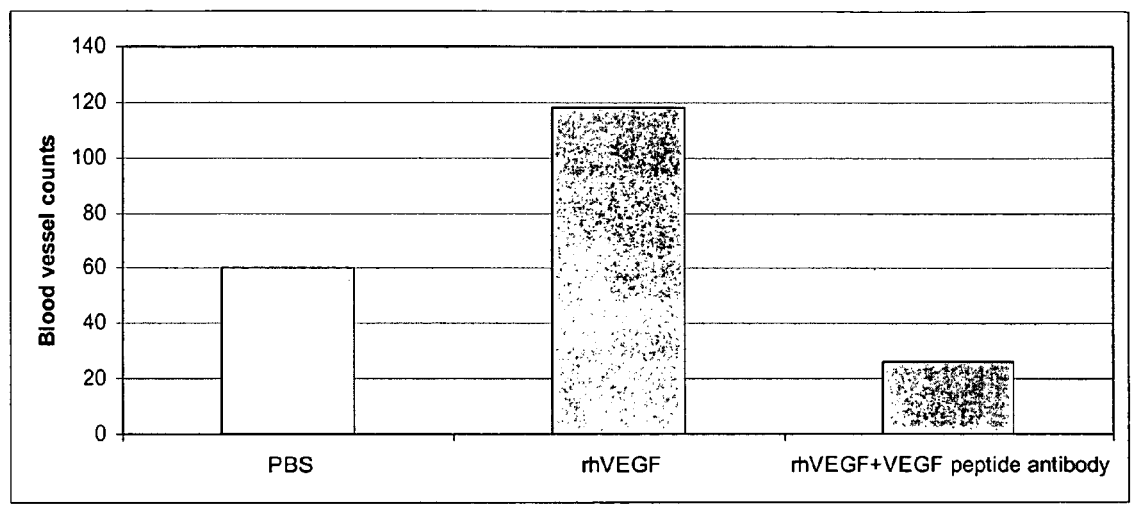
FIG. 6 shows that VEGF peptide antibodies disrupt angiogenesis into Matrigel™. C57BL/6 mice were subcutaneously injected with Matrigel™ incubated with rhVEGF, with or without VEGF peptide antibodies. After 10 days, the plugs were removed, stained, and blood vessel invasion was counted. Compared with PBS control, addition of VEGF peptide antibodies significantly disrupts angiogenesis in vivo. Each bar represents the mean (±SEM) of a group of three mice.

We went on to determine whether these VEGF peptide antibodies had anti-angiogenic properties as a result of inhibition of VEGF function. When compared with subcutaneous plugs of Matrigel™ incubated with rhVEGF prior to injection in C57BL/6 mice, plugs concurrently incubated with rhVEGF and VEGF peptide antibodies demonstrated significantly decreased angiogenesis into the Matrigel™ (P=0.005, FIGS. 5 and 6). The anti-angiogenic properties of the VEGF peptide antibodies were equivalent to that of the VEGF monoclonal antibody used as a positive control (P=NS comparing VEGF peptide antibodies to VEGF monoclonal antibodies, data not shown).

Discussion

We demonstrate that with rational peptide design employing VEGF B-cell epitopes, VEGF-specific autoantibodies are elicited. These antibodies recognized the full length protein from which the peptide was designed, and inhibit the expected protein function. Immunotherapy for cancer treatment has evolved substantially over the past decades. Previously, patients were treated with nonspecific immune stimulants, whereas currently therapy is focused on identifying specific tumor-associated antigens (TAAs) as targets for immunotherapy. Tumor-specific immunotherapy can be categorized into passive, where antibodies are targeted directly to tumor cells, and active, where vaccination with peptides, tumor cells, tumor cell lysates, carbohydrates, gene constructs, and anti-idiotpye antibodies that mimic TAAs are employed in a host that mounts a specific immune response.

Historically, active immunization with peptides has had limited efficacy because of their limited immunogenicity. Antibodies elicited in animals by immunization with synthetic peptides have generally been shown to have low affinity for the native protein, partly because antibody recognition sites are usually conformational, and the peptide immunogens lacked defined structure in solution. The genetically restricted stimulatory activity of peptides was also a major obstacle to developing vaccine approaches for use in an outbred human population [Dulofeut]. Covalent conjugation of B-cell epitope peptides to large carrier molecules was sometimes used to address this problem but often resulted in hypersensitivity, conformational changes, appearance of undefined structures, loss of epitopes, inappropriate presentation of epitopes, and batch-to-batch conjugate variability. We have addressed several of these issues in our rational approach to subunit peptide vaccine design [Dakappagari].

Our strategy involved de novo design of topographic determinants that focused on preserving the native protein sequence while facilitating folding of the peptide into a stable conformation that mimics the native protein structure [Kobs, Kaumaya 1990]. We have demonstrated the effectiveness of incorporating promiscuous T-helper epitopes derived from nonhuman molecules into these constructs to overcome human MHC genetic polymorphism [Kaumaya 1993]. Our previous work in a variety of model systems has demonstrated that this approach can elicit high-titer antibodies that recognize native protein in an outbred population, and is confirmed in this investigation of VEGF epitopes.

Importantly, subunit peptide vaccines can focus immune responses to biologically active epitopes. The need for epitope-based vaccines stems from the fact that tolerance to self-antigens, such as VEGF, may limit a functional immune response to whole protein-based vaccines due to activation of suppressor T cells that maintain tolerance to host antigens or alternate regulatory mechanisms [Sakaguchi]. The capacity to narrowly focus the immune response is of particular relevance to VEGF, where interaction of the antibody with specific sites has the potential of inhibiting growth. In contrast to passive therapy, the continuous availability of tumor-targeting antibodies can be ensured at low cost.

Previous investigators have developed similar strategies of anti-VEGF cancer therapy. Interest in VEGF as a model antigen to explore immunogene therapy has been demonstrated through the construction of a plasmid DNA encoding *Xenopus* homologous VEGF [Wei]. This group determined that immunogene tumor therapy with this vaccine led to the development of VEGF-specific antibodies that were anti-angiogenic and inhibited tumor formation. Importantly, treatment of mice with the immunogen led to no significant toxic effects. In other work, vaccination with dendritic cells transfected with VEGF mRNA has been demonstrated to lead to cytotoxic T lymphocyte (CTL) responses, to the disruption of angiogenesis, and to antitumor efficacy without significant morbidity or mortality in vivo in a murine model [Nair]. Thus, previous work has demonstrated the feasibility of active immunization using VEGF as a TAA.

Limitations of this investigation are the fact that the antigen chosen for investigation, VEGF, is ubiquitously expressed in normal and pathologic conditions, and its inhibition may lead to potentially serious biologic consequences. Although fetal development is strongly controlled by angiogenesis, only reproduction, wound healing and cancer are controlled by angiogenesis in the adult host. As such, we believe that the relative control and expression of VEGF overexpression in malignancy would lead to an acceptable therapeutic ratio in the treatment of solid tumors. This is supported by previous investigation of other methods of decreasing the effects of VEGF (i.e. through DNA vaccines or inhibition of the VEGFR) that failed to demonstrate significant toxicity.

Most women with ovarian cancer are diagnosed with advanced disease, and despite the majority obtaining a complete clinical response following induction chemotherapy, 80% will recur and succumb to their disease. This scenario suggests that microscopic residual disease after initial therapy is responsible for disease recurrence. For this reason, a current clinical research focus in the treatment of ovarian cancer is the consideration of maintenance chemotherapy. Here, following initial treatment, patients achieving a complete clinical response have been demonstrated to have a better disease-free survival when a prolonged course of treatment is initiated immediately [Markman].

Interestingly, investigation of the role of active immunization with the anti-idiotype antibody ACA125 (which imitates the tumor-associated antigen CA125 in ovarian cancer) as a maintenance chemotherapy in ovarian cancer has demonstrated a positive impact on overall survival [Wagner]. Thus, active immunization as maintenance chemotherapy to prevent symptomatic recurrence of ovarian cancer is an attractive concept. Angiogenesis has been demonstrated to influence cancer growth variably at different stages of malignant proliferation. Importantly, premalignant neoplastic conditions and small malignant tumors are thought to grow under the direct influence of endothelial mitogens such as VEGF, whereas larger malignant tumors may grow and metastasize independent of angiogenic factors [Hanahan and Folkman]. The concept that angiogenic factors control early tumor growth has been applied to the clinical management of ovarian cancer. Current research efforts are directed at investigating chemotherapy agents that may act as anti-angiogenic, cytostatic agents. These compounds, such as tamoxifen and thalidomide, are being evaluated in women with early recurrent, asymptomatic ovarian cancer to determine if anti-angiogenic therapy may prevent the development of clinically significant, symptomatic disease. As such, anti-angiogenic therapy with active immunization using VEGF epitopes could serve as a rational maintenance therapy that could significantly impact the treatment of ovarian cancer.

From this investigation, we demonstrate that rational design of peptide vaccines against VEGF leads to elicitation of high-titered VEGF peptide antibodies that are specific and anti-angiogenic.

Cited Documents for Example 1

1. Jemal A, Murray T, Samuels A, Ghafoor A, Ward E, Thun M J. Cancer statistics, 2003. CA Cancer J Clin 2003; 53:5-26.
2. McGuire W P, Hoskins W J, Brady M F, Kucera P R, Partridge E E, Look K Y, Clarke-Pearson D L, Davidson M. Cyclophosphamide and cisplatin compared with paclitaxel and cisplatin in patients with stage III and stage IV ovarian cancer. N Engl J Med 1996; 334:1-6.
3. Leung D W, Cachianes G, Kuang W J, Goeddel D V, Ferrara N. Vascular endothelial growth factor is a secreted angiogenic mitogen. Science 1989; 246:1306-9.
4. Olson T A, Mohanraj D, Carson L F, Ramakrishnan S. Vascular permeability factor gene expression in normal and neoplastic human ovaries. Cancer Res 1994; 54:276-80.
5. Boocock C A, Charnock-Jones D S, Sharkey A M, McLaren J, Barker P J, Wright K A, Twentyman P R, Smith S K. Expression of vascular endothelial growth factor and its receptors flt and KDR in ovarian carcinoma. J Natl Cancer Inst 1995; 87:506-16
6. Hollingsworth H C, Kohn E C, Steinberg S M, Rothenberg M L, Merino M J. Tumor angiogenesis in advanced stage ovarian carcinoma. Am J Pathol 1995; 147:33-41.
7. Paley P J, Staskus K A, Gebhard K, Mohanraj D, Twiggs L B, Carson L F, Ramakrishnan S. Vascular endothelial growth factor expression in early stage ovarian cancer. Cancer 1997; 80:98-106.
8. Tempfer C, Obermair A, Hefler L, Haeusler G, Gitsch G, Kainz C. Vascular endothelial growth factor serum concentrations in ovarian cancer. Obstet Gynecol 1998; 92:360-3.
9. Kim K J, Li B, Winer J, Armanini M, Gillett N, Phillips H S, Ferrara N. Inhibition of vascular endothelial growth factor-induced angiogenesis suppresses tumour growth in vivo. Nature. 1993; 362:841-4.
10. Gordon M S, Margloin K, Talpaz M, Sledge G W Jr, Holmgren E, Benjamin R, Stalter S, Shak S, Adelman D. Phase I safety and pharmacokinetic study of recombinant human anti-vascular endothelial growth factor in patients with advanced cancer. J Clin Oncol 2001; 19:843-50.
11. Margolin M, Gordon M S, Holmgren E, Gaudreault J, Fyfe G, Adelman B, Stalter S, Breed J. Phase Ib trial of intravenous recombinant humanized monoclonal antibody to vascular endothelial growth factor in combination with chemotherapy in patients with advanced cancer: Pharmacologic and long-term safety data. J Clin Oncol 2001: 19:851-6.
12. Dakappagari N, Douglas D B, Triozzi P L, Stevens V C, Kaumaya P T P. Prevention of mammary tumors with a chimeric HER-2 B-cell epitope peptide vaccine. Cancer Res 2000; 60;3782-9.
13. Peoples G E, Goedegebuure P S, Smith R, Linehan D C, Yoshino I, Eberlein T J. Breast and ovarian cancer-specific cytotoxic T lymphocytes recognize the same HER2/neu-derived peptide. Proc Natl Acad Sci USA 1995; 92:432-6.
14. Kaumaya P T P, Kobs-Conrad S, DiGeorge A M, Stevens V. De novo engineering of protein immunogenic and antigenic determinants. Peptides 1994; 9:133-64.
15. Kaumaya P T, Kobs-Conrad S, Seo Y H, Lee H, Van Buskirk A M, Feng N, Sheridan J F, Stevens V. Peptide vaccines incorporating a "promiscuous" T-cell epitope bypass certain haplotype restricted immune responses and provide broad spectrum immunogenicity. J Mol Recognit 1993; 6:81-94.
16. Passaniti A, Taylor R M, Pili R, Guo Y, Long P V, Haney J A, Pauly R R, Grant D S, Martin G R. A simple, quantitative method for assessing angiogenesis and antiangiogenic agents using reconstituted basement membrane, heparin, and fibroblast growth factor. Lab Invest 1992; 67:519-28.
17. Deulofeut H, Iglesias A, Mikael N, Bing D H, Awdeh Z, Yunis J, Marcus-Bagley D, Kruskall M S, Alper C A, Yunis E J. Cellular recognition and HLA restriction of a midsequence HBsAg peptide in hepatitis B vaccinated individuals. Mol Immunol 1993; 30:941-948.
18. Kobs-Conrad S, Lee H, DiGeorge A M, Kaumaya P T. Engineered topographic determinants with $\alpha\beta$, $\beta\alpha\beta$, and βαβα topologies show high affinity binding to native protein antigen (lactate dehydrogenase-C4). J Biol Chem 1993; 268:25285-25295.
19. Kaumaya P T, Berndt K D, Heidorn D B, Trewhella J, Kezdy F J, Goldberg E. Synthesis and biophysical characterization of engineered topographic immunogenic determinants with ααtopology. Biochemistry 1990; 29:13-23.
20. Sakaguchi S. Regulatory T cells: key controllers of immunologic self-tolerance. Cell 2000; 101:455-8.
21. Wei Y Q, Huang M J, Yang L, Zhao X, Tian L, Lu Y, Shu J M, Lu C J, Niu T, Kang B, Mao Y Q, Liu F, Wen Y J, Lei S, Luo F, Zhou L Q, Peng F, Jiang Y, Liu J Y, Zhou H, Wang Q R, He Q M, Xiao F, Lou Y Y, Xie X J, Li Q, Wu Y, Ding Z Y, Hu B, Hu M, Zhang W. Immunogene therapy of tumors with vaccine based on *Xenopus* homologous vascular endothelial growth factor as a model antigen. Proc Natl Acad Sci USA. 2001; 98:11545-50.
22. Nair S, Boczkowski D, Moeller B, Dewhirst M, Vieweg J, Gilboa E. Synergy between tumor immunotherapy and antiangiogenic therapy. Blood 2003; 102:964-71.
23. LeCouter J, Kowalski J, Foster J, Hass P, Zhang Z, Dillard-Telm L, Frantz G, Rangell L, DeGuzman L, Keller G A, Peale F, Gurney A, Hillan K J, Ferrara N. Identification of an angiogenic mitogen selective for endocrine gland endothelium. Nature. 2001; 412:877-84.
24. Markman M, Liu P Y, Wilczynski S, Monk B, Copeland L J, Alvarez R D, Jiang C, Alberts D; Southwest Oncology Group; Gynecologic Oncology Group. Phase III randomized trial of 12 versus 3 months of maintenance paclitaxel in patients with advanced ovarian cancer after complete response to platinum and paclitaxel-based chemotherapy: a Southwest Oncology Group and Gynecologic Oncology Group trial. J Clin Oncol 2003; 21:2460-5.
25. Wagner U, Kohler S, Reinartz S, Giffels P, Huober J, Renke K, Schlebusch H, Biersack H J, Mobus V, Kreienberg R, Bauknecht T, Krebs D, Wallwiener D. Immunological consolidation of ovarian carcinoma recurrences with monoclonal anti-idiotype antibody ACA125: immune responses and survival in palliative treatment. Clin Cancer Res 2001; 7:1154-1162.
26. Hanahan D, Folkman J. Patterns and emerging mechanisms of the angiogenic switch during tumorigenesis. Cell 1996; 86:353-64.

Example 2

Selection of VEGF and EG-VEGF Epitopes

The selection of candidate VEGF and EG-VEGF B-cell epitopes has been performed using computer-aided analysis using specific correlates for antigenicity employing the profiles of chain flexibility and motility, hydropathy, protrusion indices, and antigenicity. Sequences were given a score of 1 to 6 based on their respective index values and were ranked. The best scoring epitopes were further ranked by correlation with their secondary structural attributes, where an amphiphilic alpha-helical sequence or a beta-turn loop is preferred over random coil fragments. Finally, consideration was given to the individual amino acid sequence. Electrostatic ion pairs and helix dipole interaction in helical segment were also considered (hydrophobic/hydrophilic balance). The sequences receiving the highest scores were selected for further investigation. Table 1 lists the sequences and secondary structure for VEGF and EG-VEGF epitopes selected for investigation.

Our group has evaluated a number of antigenic peptides containing T-cell epitopes derived from non-human sources that have been identified to be "promiscuous" in their recognition in association with many MHC molecules and their capacity to elicit $T_H$ responses. Measles virus fusion (MVF) protein sequence 288-302 was chosen as the promiscuous epitope to overcome the challenge of tolerance and MHC polymorphism. The MVF epitope was linearly joined to the VEGF or EG-VEGF epitope by a four-residue linker (GPSL) on a peptide synthesizer. The glycine and proline residues in the linker potentiate a beta-turn in the oligopeptide, whereas the serine will favor hydrogen bonds with the free HN of the backbone. The flexible nature of the linker allows for independent folding of the T- and B-cell epitopes. Peptides were purified by reverse-phase HPLC to ensure >95% purity. The identity of the peptides was performed by matrix-assisted LASER desorption ionization-time of flight spectrometry.

Figure 7:
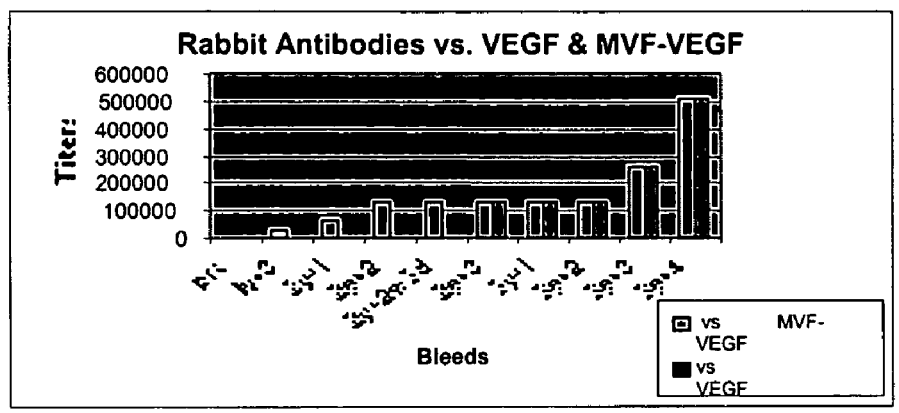
FIG. 7 is a graph showing rabbit anti-peptide antibodies against immunogenic epitopes of (A) VEGF and (B) EG-VEGF, with and without the addition of the measles virus fusion protein (MVF)
Figure 7:
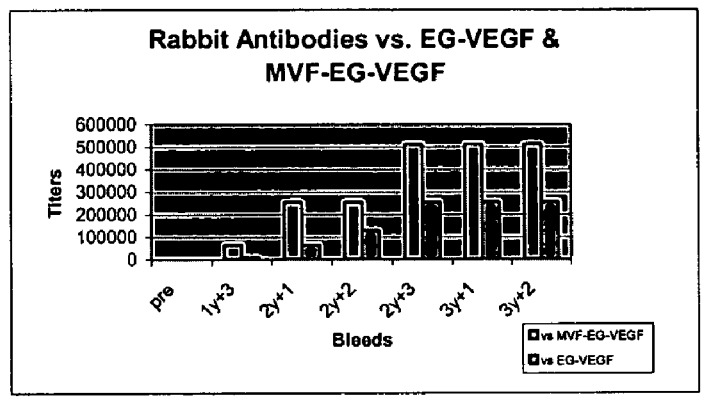

To generate anti-VEGF and anti-EG-VEGF antibodies, rabbits were immunized subcutaneously at multiple sites with a total of 1 mg of each peptide emulsified in a Squaline/Arlacel vehicle containing nor-MDP (N-acetyl-glucosamine-3 yl-acetyl L-alanyl-D-isoglutamine). Subsequent booster injections were given at 3 and 6 weeks after primary immunization. Rabbit sera was obtained weekly and purified, and quantified by ELISA (FIG. 7).

Following the purification of anti-VEGF and anti-EG-VEGF antibodies, we went on to determine whether the elicited antibodies had anti-angiogenic properties. Previous data demonstrates that ovarian function is tightly regulated through angiogenic stimuli, and VEGF has been shown to be important in the recruitment and selection of follicles. We thus hypothesized that if the antibodies were functioning as anti-angiogenic molecules, then inhibition of follicle selection and growth and estrous cycle disruption would be expected with neutralization of VEGF.

Figure 8:
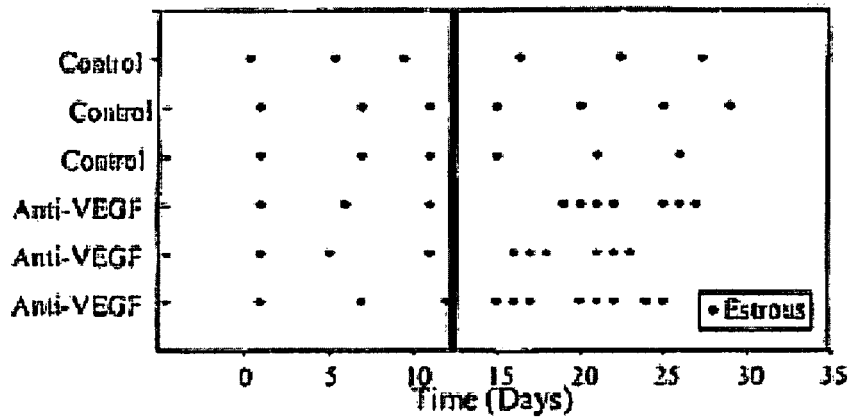
FIG. 8 shows disruption of (A) and shortening of (B) cyclic estrous cycles as well as (C) a decrease in the number of primordial follicles with passive immunization with anti-VEGF antibodies in a murine model.
Figure 8:
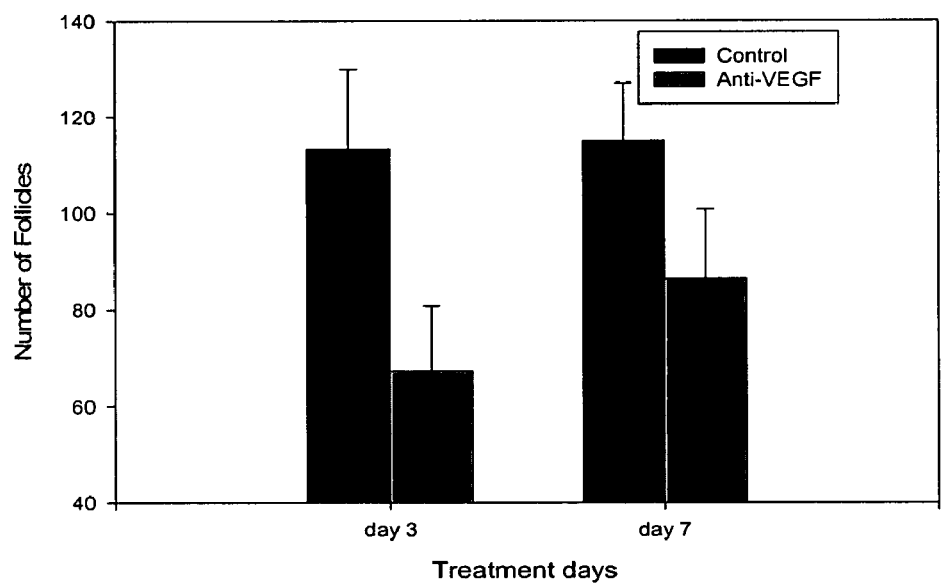

Thirteen female C57BL/6 mice were injected intraperitoneally with 25 μg of purified anti-VEGF antibody every 3 days for 15 days. Estrous cycles were monitored by obtaining daily vaginal smears, and the estrous cycles of treated mice were compared with control mice injected with nonspecific IgG antibodies. In keeping with the anti-angiogenic effect of elicited anti-VEGF antibodies, a significant disruption of the established estrous cycle was seen beginning day 3 following immunization (FIG. 8A). The average length of the estrous cycles was also significantly decreased by over 66% (FIG. 8B). Primordial follicle growth was assessed at day 3 and day 7 following immunization by harvesting the ovaries of euthanized mice. A significant and persistent reduction in the number of primordial follicles (p<0.05 for both comparisons) was demonstrated in mice treated with anti-VEGF antibodies, suggesting potent anti-angiogenic efficacy of the VEGF antibodies (FIG. 8C).

Collectively, these data demonstrated that immunogenic epitopes of VEGF and EG-VEGF can be identified and synthesized, and immunization leads to production of anti-VEGF and anti-EG-VEGF antibodies. Such antibodies are biologically active, and function as anti-angiogenic molecules.

Figure 9:
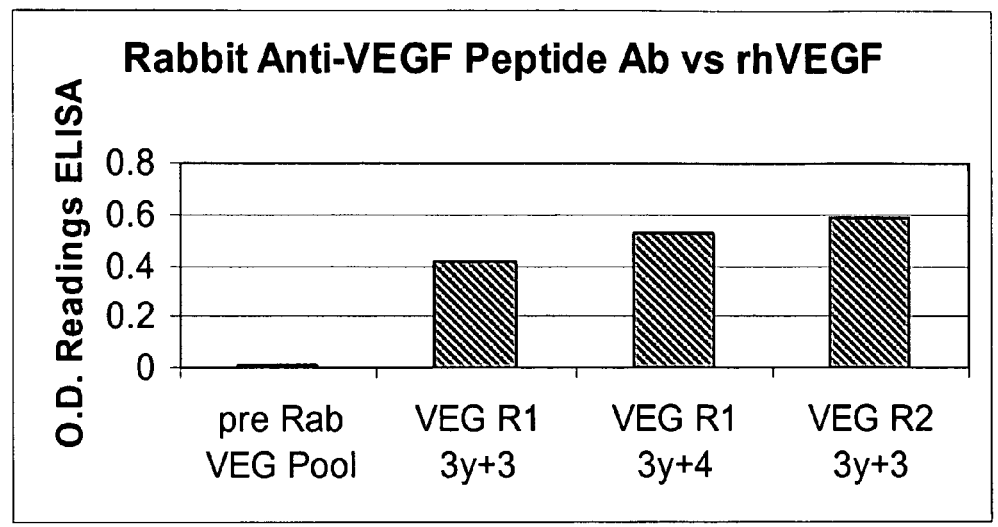
FIG. 9 shows that (A) Anti-VEGF and (B) anti-EG-VEGF peptide antibodies recognize rhVEGF and rhEG-VEGF.
Figure 9:
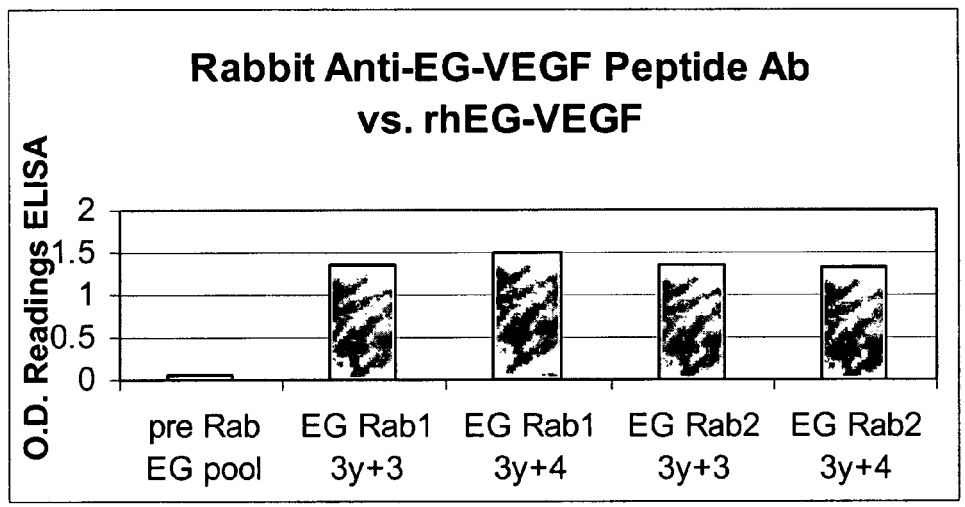

Determination of Immunogenicity of Anti-VEGF and Anti-EG-VEGF Antibodies Elicited from Active Immunization with Peptide Vaccines ELISA demonstrated anti-VEGF and anti-EG-VEGF peptide antibodies to recognize the respective recombinant human VEGF (FIG. 9A) or EG-VEGF protein (FIG. 9B). In this experiment, recombinant proteins were used to coat ELISA plates, and the appropriate anti-peptide antibody was used.

Figure 10:
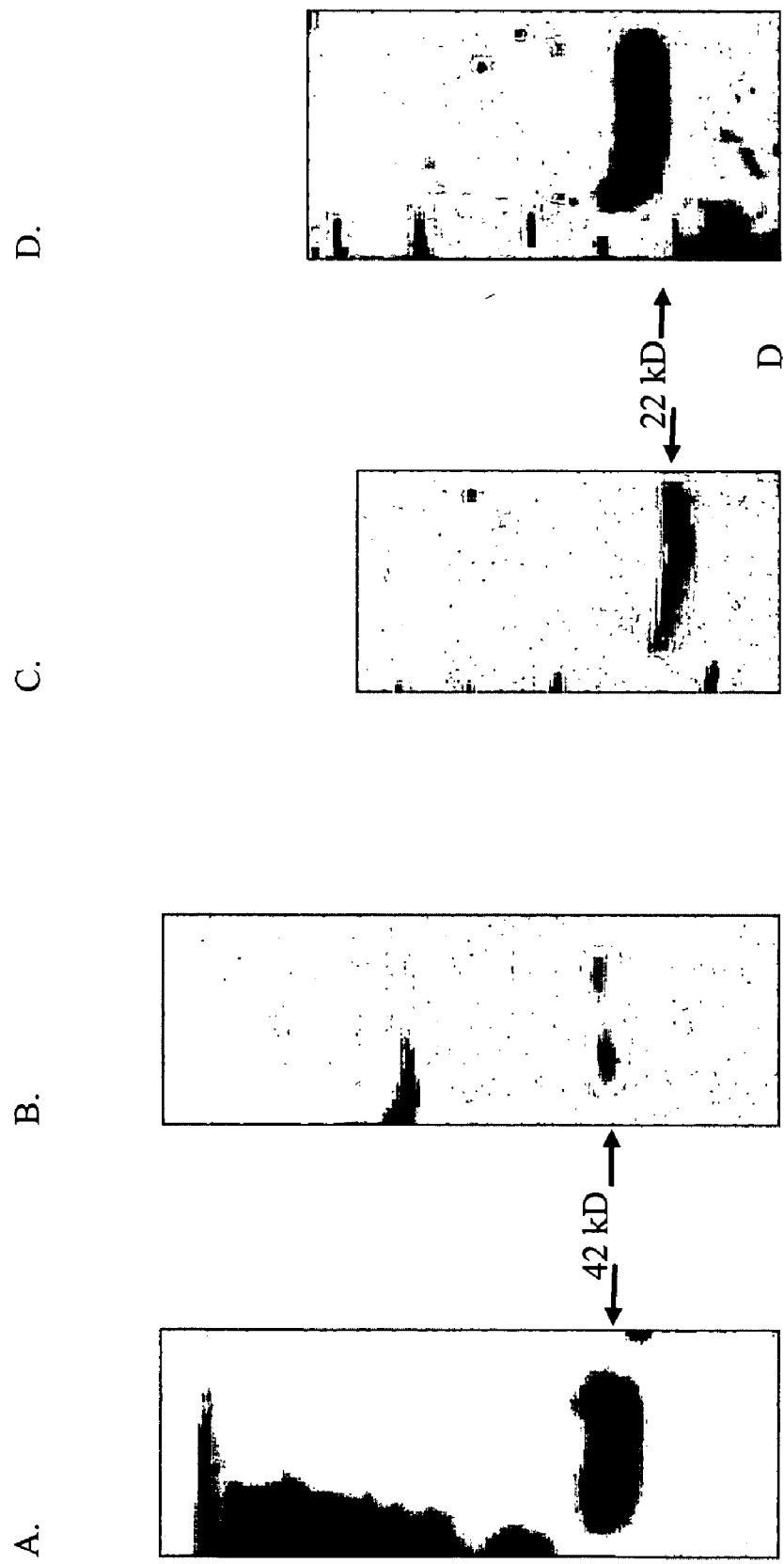
FIG. 10 shows Western blots of rhVEGF (A and B) blotted with (A) anti-VEGF peptide antibody and (B) Ab-4, a monoclonal anti-VEGF antibody. Western blot of rhEG-VEGF (C and D), blotted with (C) rabbit anti-EG-VEGF peptide antibody and (D) rabbit anti-VEGF/anti-peptide EG-VEGF "combination" antibody, all demonstrating recognition of the appropriate recombinant protein.

Furthermore, we demonstrated that the anti-VEGF and anti-EG-VEGF peptide antibodies recognize rhVEGF by Western blot, with the resultant bands in the expected location (42 kD, dimer) for VEGF blotted with anti-VEGF peptide antibody (FIG. 10A) and VEGF monoclonal antibody (Neo-Markers Ab-4, FIG. 10B). Likewise, a Western blot with rhEG-VEGF blotted with anti-EG-VEGF peptide antibodies (FIG. 10C) and a combination anti-VEGF/anti-EG-VEGF peptide antibody (FIG. 10D) resulted in a band in the expected location (22 kD, dimer) for rhEG-VEGF.

Assessment of in vitro Biologic Effect of Anti-VEGF and Anti-EG-VEGF Peptide Antibodies Following demonstration of the antigenic and immunogenic properties of our anti-peptide antibodies, we went on to evaluate the functional properties of these molecules. In an effort to determine the effect of our anti-VEGF peptide antibodies on the interaction of VEGF with the VEGF receptor, we used the Fluorokine assay. Briefly, washed cells are incubated with the biotinylated cytokine that in turn binds to the cells via specific cell surface receptors. The cells are then directly incubated with avidin-fluorescein, which attaches to the receptor bound biotinylated cytokine. Unbound biotinylated cytokine participates in an amplification reaction with the bound cytokine that results in an enhanced signal without compromising specificity.

Figure 11:
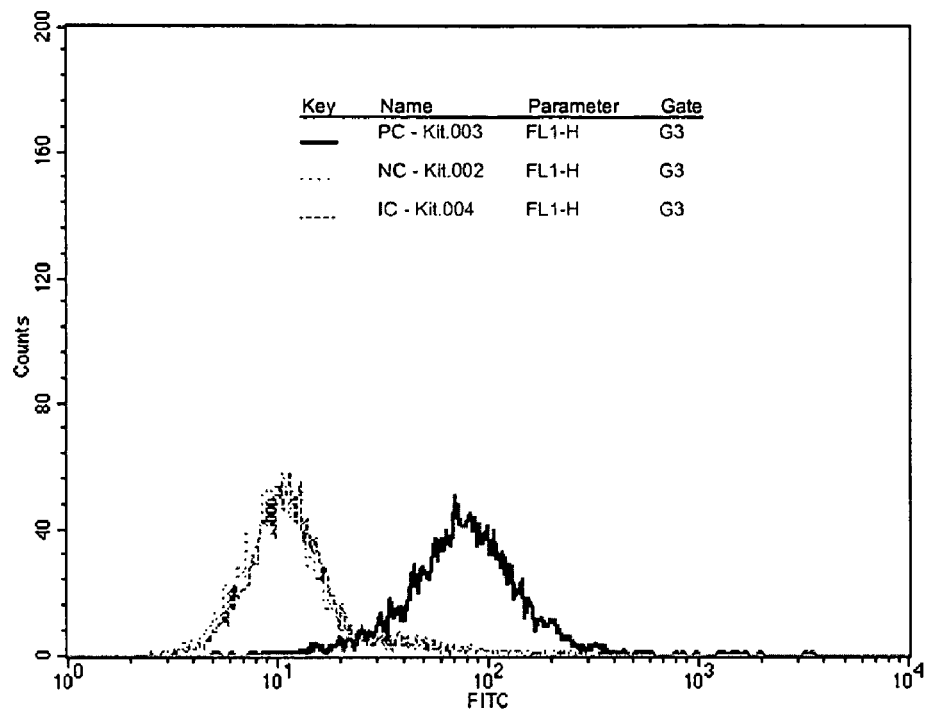
FIG. 11 shows the results of a Fluorokine assay for evaluation of the functional properties of anti-VEGF peptide antibodies. (A) Evaluation of the positive (PC), negative (NC) and inhibitor antibody (IC) controls of Fluorokine assay, and (B) the same PC and NC as in (A), and employing either mouse or rabbit anti-VEGF peptide antibodies, as well as the combination anti-VEGF/anti-EG-VEGF peptide antibody, all demonstrating disruption of the VEGF-VEGF receptor interaction.
Figure 11:
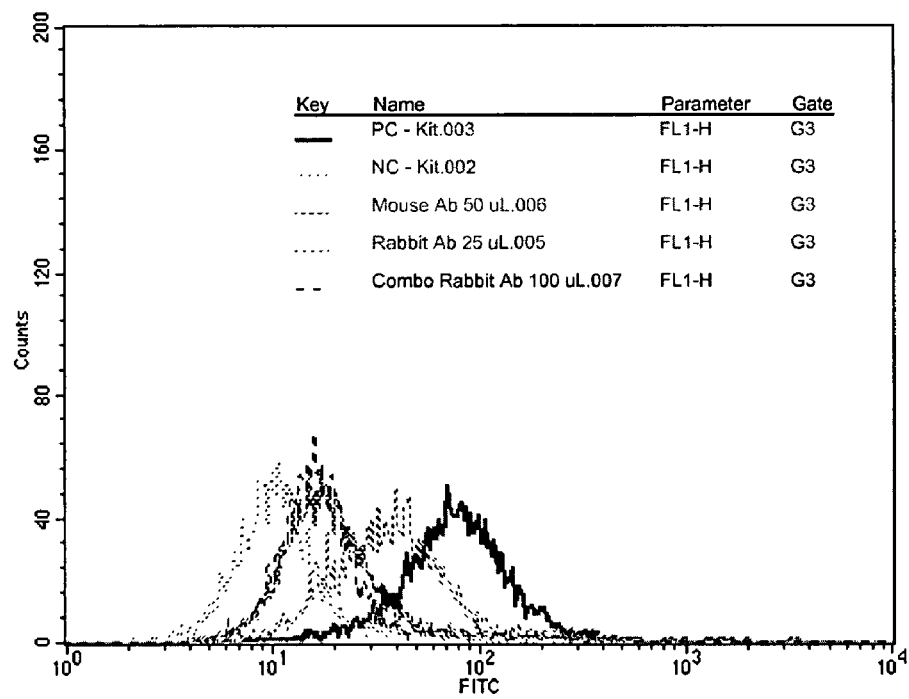
Figure 12:
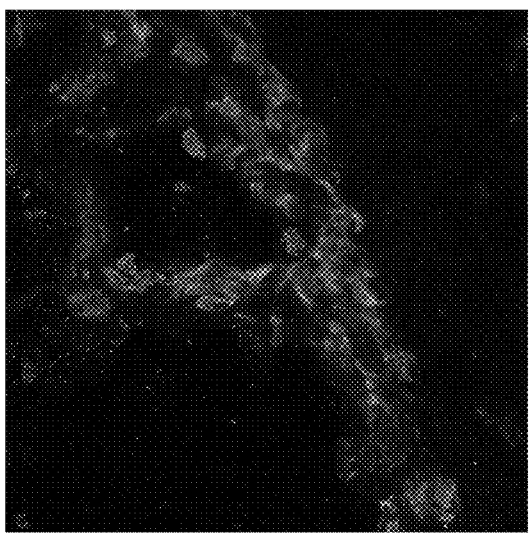
FIG. 12 shows injection of (A) subcutaneous matrigel and (B) subcutaneous matrigel combined with rhVEGF, stained with CD31:phycoerythrin conjugate antibody demonstrates increased angiogenesis in C57/BL6 mice.
Figure 12:
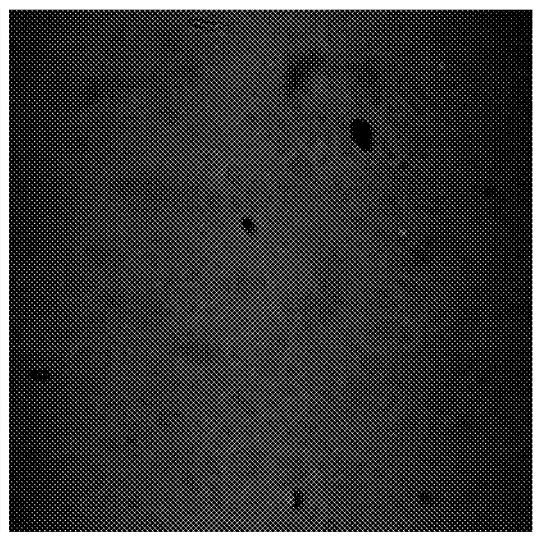

Cells expressing the specific cytokine receptors are fluorescently stained, with the intensity of staining proportional to the density of the receptors. Relative receptor density is then determined by flow cytometric analysis using 488 nm wavelength laser excitation. Through this experiment, we initially standardized the flow cytometry component of the assay (FIG. 11A), in which different cell populations were identified using the kit supplied positive and negative controls. Following standardization, we used HUVEC cells that proliferate under the influence of VEGF to determine the efficacy of binding of our anti-peptide antibodies to VEGF, resulting in disruption of the normal VEGF-VEGF receptor interaction. As can be seen in (FIG. 11B), a shift in population toward decreased receptor density is demonstrated when anti-VEGF peptide antibodies are used, suggesting a disruption in the normal VEGF-VEGF receptor interaction.

Assessment of Anti-Angiogenic In Vivo Biologic Effect of Anti-VEGF Peptide Vaccines Although we have demonstrated the interaction between VEGF and our anti-peptide VEGF antibodies, it is still important to determine whether the effect of this interaction leads to a modification of angiogenic properties of VEGF. To determine the anti-angiogenic properties of our antibodies, we injected subcutaneous matrigel (basement membrane generated from EHS sarcoma) into immunocompetent C57/BL6 mice, with or without rhVEGF. The matrigel was removed after 7 days, and cryostat sections were cut and stained with a conjugate of CD31 (which binds to endothelial cells) and phycoerythrin. Angiogenesis was qualitatively and quantitatively determined through fluorescence confocal microscopy. The addition of rhVEGF to the matrigel led to a significant increase in angiogenesis relative to control.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

What is claimed is:

1. A peptide comprising:
   a) at least one VEGF epitope consisting of amino acids 102 through 122 of SEQ ID NO: 1;
   b) a helper T cell epitope selected from the group consisting of TT (SEQ ID NO: 3), TT1 (SEQ ID NO: 4), P2 (SEQ ID NO: 5), P30 (SEQ ID NO: 6), MVF (SEQ ID NO: 7), HBV (SEQ ID NO: 8), and CSP (SEQ ID NO: 9); and
   c) a linker consisting of Gly-Pro-Ser-Leu (SEQ ID NO: 10) joining the at least one VEGF epitope to the helper T cell epitope,
   wherein the linker is operatively linked to the C-terminus of the at least one VEGF epitope and operatively linked to the N-terminus of the helper T cell epitope.

2. The peptide according to claim 1, wherein the helper T cell epitope is MVF (SEQ ID NO: 7).

3. An immunogenic composition comprising the peptide according to claim 1, and at least one pharmacologically acceptable carrier.

4. A polynucleotide which encodes the peptide according to claim 1.

* * * * *

SEQUENCE LISTING

<160> NUMBER OF SEQ ID NOS: 10

<210> SEQ ID NO 1
<211> LENGTH: 190
<212> TYPE: PRT
<213> ORGANISM: Homo sapiens

<400> SEQUENCE: 1

```
Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
             35                  40                  45

Arg Ser Tyr Cys His Pro Ile Glu Thr Leu Asp Ile Phe Gln Glu Tyr
         50                  55                  60

Pro Asp Glu Ile Glu Tyr Ile Phe Lys Pro Ser Cys Val Pro Leu Met
 65                  70                  75                  80

Arg Cys Gly Gly Cys Ser Asn Asp Glu Gly Leu Glu Cys Val Pro Thr
                 85                  90                  95

Glu Glu Ser Asn Ile Thr Met Gln Ile Met Arg Ile Lys Pro His Gln
            100                 105                 110

Gly Gln His Ile Gly Glu Met Ser Phe Leu Gln His Asn Lys Cys Glu
        115                 120                 125

Cys Arg Pro Lys Lys Asp Arg Ala Arg Gln Glu Asn Pro Cys Gly Pro
    130                 135                 140
```

Cys Ser Glu Arg Arg Lys His Leu Phe Val Gln Asp Pro Gln Thr Cys
145                 150                 155                 160

Lys Cys Ser Cys Lys Asn Thr His Ser Arg Cys Lys Ala Arg Gln Leu
            165                 170                 175

Glu Leu Asn Glu Arg Thr Cys Arg Cys Asp Lys Pro Arg Arg
            180                 185                 190

<210> SEQ ID NO 2
<211> LENGTH: 105
<212> TYPE: PRT
<213> ORGANISM: Homo sapiens

<400> SEQUENCE: 2

Met Arg Gly Ala Thr Arg Val Ser Ile Met Leu Leu Leu Val Thr Val
1               5                   10                  15

Ser Asp Cys Ala Val Ile Thr Gly Ala Cys Glu Arg Asp Val Gln Cys
            20                  25                  30

Gly Ala Gly Thr Cys Cys Ala Ile Ser Leu Trp Leu Arg Gly Leu Arg
            35                  40                  45

Met Cys Thr Pro Leu Gly Arg Glu Gly Glu Cys His Pro Gly Ser
    50                  55                  60

His Lys Val Pro Phe Phe Arg Lys Arg Lys His His Thr Cys Pro Cys
65                  70                  75                  80

Leu Pro Asn Leu Leu Cys Ser Arg Phe Pro Asp Gly Arg Tyr Arg Cys
            85                  90                  95

Ser Met Asp Leu Lys Asn Ile Asn Phe
            100                 105

<210> SEQ ID NO 3
<211> LENGTH: 19
<212> TYPE: PRT
<213> ORGANISM: Clostridium tetani

<400> SEQUENCE: 3

Asn Ser Val Asp Asp Ala Leu Ile Asn Ser Thr Ile Tyr Ser Tyr Phe
1               5                   10                  15

Pro Ser Val

<210> SEQ ID NO 4
<211> LENGTH: 17
<212> TYPE: PRT
<213> ORGANISM: Clostridium tetani

<400> SEQUENCE: 4

Pro Gly Ile Asn Gly Lys Ala Ile His Leu Val Asn Asn Gln Ser Ser
1               5                   10                  15

Glu

<210> SEQ ID NO 5
<211> LENGTH: 15
<212> TYPE: PRT
<213> ORGANISM: Clostridium tetani

<400> SEQUENCE: 5

Gln Tyr Ile Lys Ala Asn Ser Lys Phe Ile Gly Ile Thr Glu Leu
1               5                   10                  15

<210> SEQ ID NO 6
<211> LENGTH: 21
<212> TYPE: PRT

```
<213> ORGANISM: Clostridium tetani

<400> SEQUENCE: 6

Phe Asn Asn Phe Thr Val Ser Phe Trp Leu Arg Val Pro Lys Val Ser
 1               5                  10                  15

Ala Ser His Leu Glu
            20

<210> SEQ ID NO 7
<211> LENGTH: 15
<212> TYPE: PRT
<213> ORGANISM: Measles virus

<400> SEQUENCE: 7

Leu Ser Glu Ile Lys Gly Val Ile Val His Arg Leu Glu Gly Val
 1               5                  10                  15

<210> SEQ ID NO 8
<211> LENGTH: 15
<212> TYPE: PRT
<213> ORGANISM: Hepatitis B virus

<400> SEQUENCE: 8

Phe Phe Leu Leu Thr Arg Ile Leu Thr Ile Pro Gln Ser Leu Asn
 1               5                  10                  15

<210> SEQ ID NO 9
<211> LENGTH: 20
<212> TYPE: PRT
<213> ORGANISM: Plasmodium vivax

<400> SEQUENCE: 9

Thr Cys Gly Val Gly Val Arg Val Arg Ser Arg Val Asn Ala Ala Asn
 1               5                  10                  15

Lys Lys Pro Glu
            20

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 10

Gly Pro Ser Leu
 1
```